United States Patent
Docherty et al.

(10) Patent No.: US 9,775,508 B1
(45) Date of Patent: Oct. 3, 2017

(54) DEPOLARIZING REGION IDENTIFICATION IN THE RETINA

(71) Applicant: CANON KABUSHIKI KAISHA, Tokyo (JP)

(72) Inventors: Andrew Docherty, Surry Hills (AU); Barry James Drake, Thornleigh (AU)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 15/148,795

(22) Filed: May 6, 2016

(51) Int. Cl.
| | |
|---|---|
| *G02B 3/14* | (2006.01) |
| *G02B 3/00* | (2006.01) |
| *A61B 3/00* | (2006.01) |
| *G06T 7/00* | (2017.01) |
| *G06K 9/62* | (2006.01) |
| *G06K 9/52* | (2006.01) |
| *A61B 3/10* | (2006.01) |
| *A61B 3/12* | (2006.01) |

(52) U.S. Cl.
CPC ............ *A61B 3/0025* (2013.01); *A61B 3/102* (2013.01); *A61B 3/1225* (2013.01); *G06K 9/52* (2013.01); *G06K 9/6267* (2013.01); *G06T 7/0012* (2013.01); *G06T 2207/10072* (2013.01); *G06T 2207/30041* (2013.01)

(58) Field of Classification Search
CPC .................................... A61B 3/14; A61B 3/00
USPC .................................................. 351/206, 246
See application file for complete search history.

(56) References Cited

PUBLICATIONS

Baumann, B., et al., "Segmentation and quantification of retinal lesions in age-related macular degeneration using polarization-sensitive optical coherence tomography", J. Biomed Opt., 2010, vol. 15, No. 16.

Gotzinger, E., et al., "Retinal pigment epithelium segmentation by polarization sensitive optical coherence tomography", Opt Express., Oct. 13, 2008, pp. 16410-16422, vol. 16, No. 21.

*Primary Examiner* — Jack Dinh
(74) *Attorney, Agent, or Firm* — Canon USA Inc., IP Division

(57) ABSTRACT

A computer-implementable method of analyzing tissues of a retina. A polarization-sensitive (PS-OCT) image data set of the retina is received from a polarization-sensitive device, each element in the polarization-sensitive image data set being associated with an intensity value ($\{I_1, \ldots, I_L\}$) and a polarization direction ($\{P_1, \ldots, P_L\}$). A likelihood score is determined for each element of the polarization-sensitive image data set based on the intensity value of the element and a degree of divergence ($\mu^{*T}P$ or $D_2$) of the polarization direction associated with the element from a reference polarization direction ($\mu^*$) associated with the polarization sensitive image data set, wherein the likelihood score indicates whether said element is drawn from a directionally polarized distribution or a depolarizing distribution. Elements of the polarization-sensitive image data set are classified using the determined likelihood scores to analyze tissues of the retina.

18 Claims, 20 Drawing Sheets

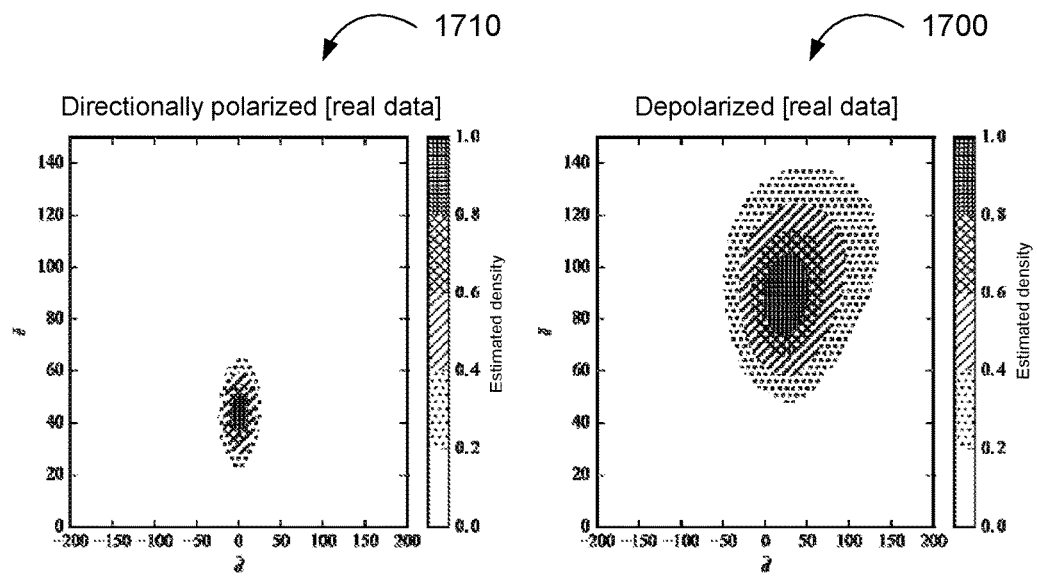
Fig. 17A  Fig. 17B
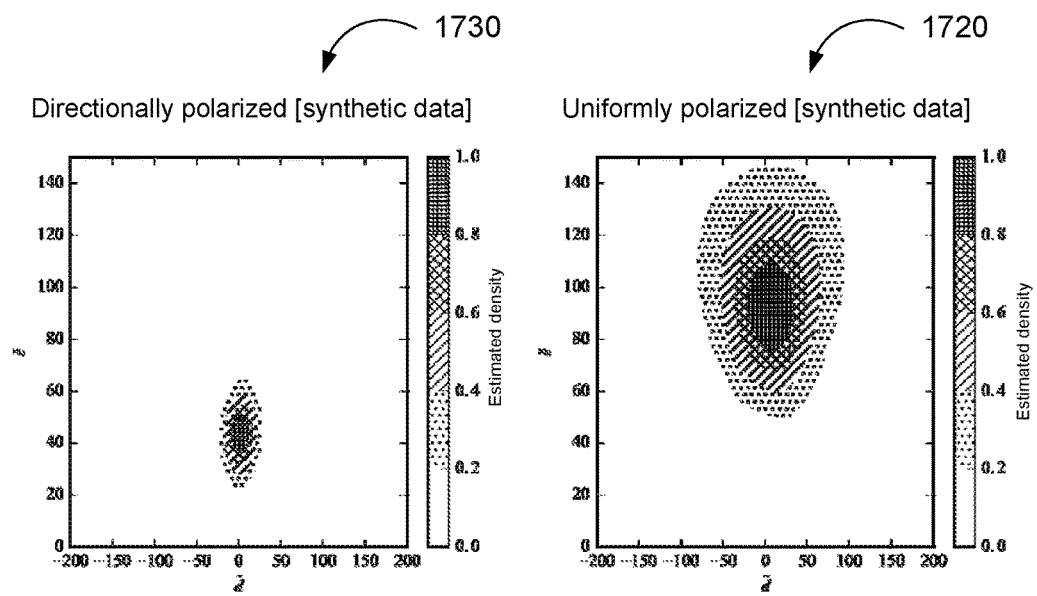
Fig. 17C  Fig. 17D

DEPOLARIZING REGION IDENTIFICATION IN THE RETINA

TECHNICAL FIELD

The current invention relates to generally to methods for optical imaging of biological samples and for the processing of such images. In particular, the present invention relates to a method for estimating the depolarization of biological tissues using polarization sensitive imaging techniques.

BACKGROUND

Optical coherence tomography (OCT) is a medical imaging technique for non-invasive imaging based on low-coherence interferometry employing near-infrared light. The OCT device produces three-dimensional (3D) images, with a resolution typically of a few microns, and is widely used in ophthalmology due to the translucent nature of the human eye and the ability to resolve details in the structure of the retina that are important in eye pathology.

Spectral-domain OCT (SD-OCT) is a form of OCT in which the interferometric signal between a reference beam and the back-scattered component of a sample (probe) beam directed into the retina is split into its frequency components by a dispersive device and collected by a line camera. The collected data contains the spectral information of the back-scattered signal. This spectral data can be transformed to the spatial domain to obtain a one-dimensional (1D) spatial distribution, referred to as an A-scan, representative of the scattering properties of the sample. Scanning the sample beam across the retina, produces a series of adjacent A-scans which can then be used to create a two-dimensional (2D) tomogram, called a B-scan. A volume representation can be acquired by further scanning the sample beam in a third direction to collect a series of B-scans that covers the three-dimensional (3D) volume of interest.

The OCT signal measures the reflectivity and absorption of the biological tissues. However, determining the functional properties of such tissues is as important as the structure revealed by the backscattered intensity. In recent years, functional extensions of OCT have been investigated that can provide further information. For example, Doppler OCT can provide information about blood flow, and Polarization-Sensitive OCT (PS-OCT) can provide information about the polarization properties of the tissues.

Polarization-Sensitive OCT provides information about the polarization properties of turbid media. The eye has many structures that have useful polarization properties that have been the subject of PS-OCT research, for example the birefringence of the retinal nerve fiber layer (RNFL) has been suggested to be linked to the microtubule density. In addition to birefringence, polarization-preserving and polarization-scrambling structures can be distinguished by PS-OCT. This property has been used to identify the retinal pigment epithelium (RPE) tissue layer in the retina by identifying the polarization scrambling layer located near the RPE. The RPE is of significant importance to vision and damage or distortion of the RPE is associated with age-related macular degeneration (AMD) and progressive loss of vision.

Polarization scrambling tissues in the retina, such as the RPE, cause back-scattered light to be depolarized. Measuring the degree of such depolarization is an important function of a PS-OCT device when identification of RPE tissue is required. Measuring the depolarization, typically requires receiving multiple estimates of the polarization state of back-scattered light from the same location in the retina at different times. The degree to which these measurements differ can be used as a measure of the depolarization of the light.

However, in an OCT device it is currently difficult to record multiple measurements at the same location when measuring a volume. This is due to the limited speed of OCT capture and to the motion of the retina while capture is taking place. This leads to a choice of sampling the same point multiple times in a fixed time by limiting the resolution of the captured volume, or taking a longer time to sample the volume at the same resolution leading to greater distortion in the sampled volume. Therefore, it is preferable to have a method of determining the degree of polarization in a PS-OCT volume scan without repeated measurement of the same location.

In recent years, a measure of the depolarization of back-scattered light in a PS-OCT device has been demonstrated by extending the concept of the degree of polarization to a spatial region. This is called the degree of polarization uniformity, DOPU, and measures the degree of spatial change in the back-scattered polarization signal. However, DOPU can only be calculated in regions that have a high intensity, and the size of the spatial region used to calculate the DOPU causes a change in the size of the region that appears to be depolarizing (i.e. polarization scrambling).

Therefore, there is still a need for a method for measuring the depolarization of regions within OCT scans that overcomes these problems.

SUMMARY

It is an object of the present invention to substantially overcome, or at least ameliorate, one or more disadvantages of existing arrangements.

According to one aspect of the present disclosure, there is provided a computer-implementable method of analysing tissues of a retina, the method comprising:

receiving a polarization-sensitive (PS-OCT) image data set of the retina from a polarization-sensitive device, each element in the polarization-sensitive image data set being associated with an intensity value ($\{I_1, \ldots, I_L\}$) and a polarization direction ($\{P_1, \ldots, P_L\}$);

determining a likelihood score for each element of the polarization-sensitive image data set based on the intensity value of the element and a degree of divergence ($\mu^{*T}P$ or $D_2$) of the polarization direction associated with the element from a reference polarization direction ($\mu^*$) associated with the polarization sensitive image data set, wherein the likelihood score indicates whether said element is drawn from a directionally polarized distribution or a depolarizing distribution; and classifying elements of the polarization-sensitive image data set using the determined likelihood scores to analyse tissues of the retina.

According to another aspect of the present disclosure, there is provided a system for analysing tissues of a retina, the system comprising:

a memory for storing data and a computer program;

a processor coupled to the memory for storing data and a computer program, the computer program comprising instructions for:

receiving a polarization-sensitive (PS-OCT) image data set of the retina from a polarization-sensitive device, each element in the polarization-sensitive image data set being associated with an intensity value ($\{I_1, \ldots, I_L\}$) and a polarization direction ($\{P_1, \ldots, P_L\}$);

determining a likelihood score for each element of the polarization-sensitive image data set based on the intensity value of the element and a degree of divergence ($\mu^{*T}P$ or $D_2$) of the polarization direction associated with the element from a reference polarization direction ($\mu^*$) associated with the polarization sensitive image data set, wherein the likelihood score indicates whether said element is drawn from a directionally polarized distribution or a depolarizing distribution; and classifying elements of the polarization-sensitive image data set using the determined likelihood scores to analyse tissues of the retina.

According to another aspect of the present disclosure, there is provided an apparatus for analysing tissues of a retina, the apparatus comprising:

means for receiving a polarization-sensitive (PS-OCT) image data set of the retina from a polarization-sensitive device, each element in the polarization-sensitive image data set being associated with an intensity value ($\{I_1, \ldots, I_L\}$) and a polarization direction ($\{P_1, \ldots, P_L\}$);

means for determining a likelihood score for each element of the polarization-sensitive image data set based on the intensity value of the element and a degree of divergence ($\mu^{*T}P$ or $D_2$) of the polarization direction associated with the element from a reference polarization direction ($\mu^*$) associated with the polarization sensitive image data set, wherein the likelihood score indicates whether said element is drawn from a directionally polarized distribution or a depolarizing distribution; and means for classifying elements of the polarization-sensitive image data set using the determined likelihood scores to analyse tissues of the retina.

According to still another aspect of the present disclosure, there is provided a computer readable medium having a computer program stored thereon for analysing tissues of a retina, the program comprising:

code for receiving a polarization-sensitive (PS-OCT) image data set of the retina from a polarization-sensitive device, each element in the polarization-sensitive image data set being associated with an intensity value ($\{I_1, \ldots, I_L\}$) and a polarization direction ($\{P_1, \ldots, P_L\}$);

code for determining a likelihood score for each element of the polarization-sensitive image data set based on the intensity value of the element and a degree of divergence ($\mu^{*T}P$ or $D_2$) of the polarization direction associated with the element from a reference polarization direction ($\mu^*$) associated with the polarization sensitive image data set, wherein the likelihood score indicates whether said element is drawn from a directionally polarized distribution or a depolarizing distribution; and code for classifying elements of the polarization-sensitive image data set using the determined likelihood scores to analyse tissues of the retina.

According to still another aspect of the present disclosure, there is provided a computer-implementable method of determining physical properties of tissues of a retina, the method comprising:

receiving a polarization-sensitive image data set of the retina from a polarization-sensitive device, each element in the polarization-sensitive image data set being associated with an intensity value and polarization data;

determining, for each element of the polarization-sensitive image data set, a likelihood score (D) that said element is drawn from a polarization scrambling signal based on a reference polarization direction ($\mu^*$) associated with the polarization-sensitive image data set, the intensity value and the polarization data of the element; and classifying the elements of the polarization-sensitive image data set using the determined likelihood scores to determine physical properties of tissues of the retina.

BRIEF DESCRIPTION OF THE DRAWINGS

At least one embodiment of the present invention will now be described with reference to the following drawings, in which:

FIGS. 17A and 17B show graphical representations of the histograms for directionally polarized and uniformly polarized data estimated from acquired PS-OCT data, as calculated using the method of FIG. 15;

FIGS. 17C and 17D show graphical representations of the histograms for directionally polarized and uniformly polarized data estimated from synthetically generated polarization data, as calculated using the method of FIG. 15;

DETAILED DESCRIPTION INCLUDING BEST MODE

Overview

Polarization scrambling tissues in the retina, such as the RPE, cause back-scattered light to be randomly polarized. Measuring the degree of such randomness is an important function of a PS-OCT device when identification of RPE tissue is required. However, due to noise inherent in the detection process the detected polarization will have some degree of randomness even for signals scattered from tissues that do not scramble the polarization.

According to the present disclosure, a Bayesian approach is used to distinguish between the polarization randomness caused by detection noise and the polarization randomness caused by polarization scrambling. The present inventors have found that a Bayesian approach improves on the current state-of-the-art for calculating the depolarization of a signal as it allows the incorporation of known system characteristics, including distributions of polarization and detection (system) noise, in a systematic way. Using these system characteristics, and a polarization direction determined from the input polarization data, a logarithmic score is determined that is related to the ratio of the probability that the signal is scattered from polarization scrambling tissue versus polarization maintaining tissue. These logarithmic scores can be combined linearly using standard linear filters.

Context

Figure 1:
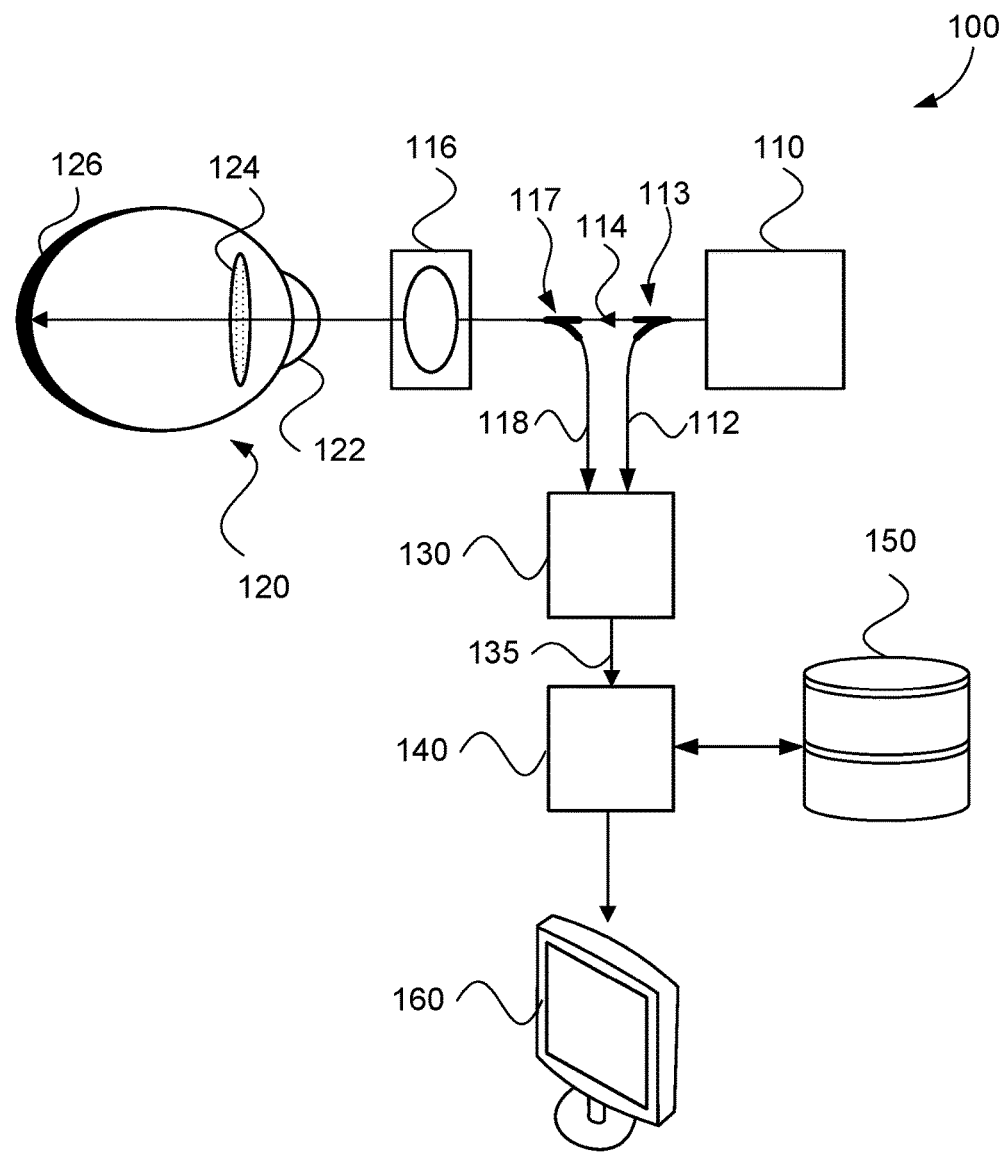
FIG. 1 is a schematic block diagram of a PS-OCT system with depolarization score processing.

FIG. 1 shows an example of a PS-OCT system (100) including a signal processing unit (140) for the processing of the acquired data. The PS-OCT system (100) has a superluminescent diode or other low-coherence light source (110). The source light (110) is split into a reference beam (112) and a probe (sample) beam (114) by a beam splitter (113). The probe beam (114) is directed through a controllable lens (116) into the anterior (122) of the eye (120). The probe beam (114) is typically circularly polarized. The controllable lens (116) is used to focus the probe beam (114) onto the retina (126) of the eye (120) compensating for differences in the optical characteristics of the eye (120), including the lens (124) and anterior (122). The light directed to the eye (120) is backscattered, predominantly from the retina (126) and is directed back to the PS-OCT system (100) through a beam splitter (117) where the remaining backscattered signal (118) is combined with the reference beam (112) and detected by a PS-OCT detector (130). The PS-OCT detector (130) is a polarization-sensitive device which splits the backscattered signal (118) into two orthogonal polarizations and converts the spectrum of the signal to electrical signals, generally by dispersing the backscattered signal by a dispersive element and detecting the intensity using a line detector with a number of detector elements. Detected PS-OCT signals (135) output from the detector (130) for an OCT scan of the eye (120) form a polarization-sensitive image data set of the retina which can be further processed by a computational unit (140) and stored on a storage unit (150), and optionally displayed on display unit (160).

Figure 2A:
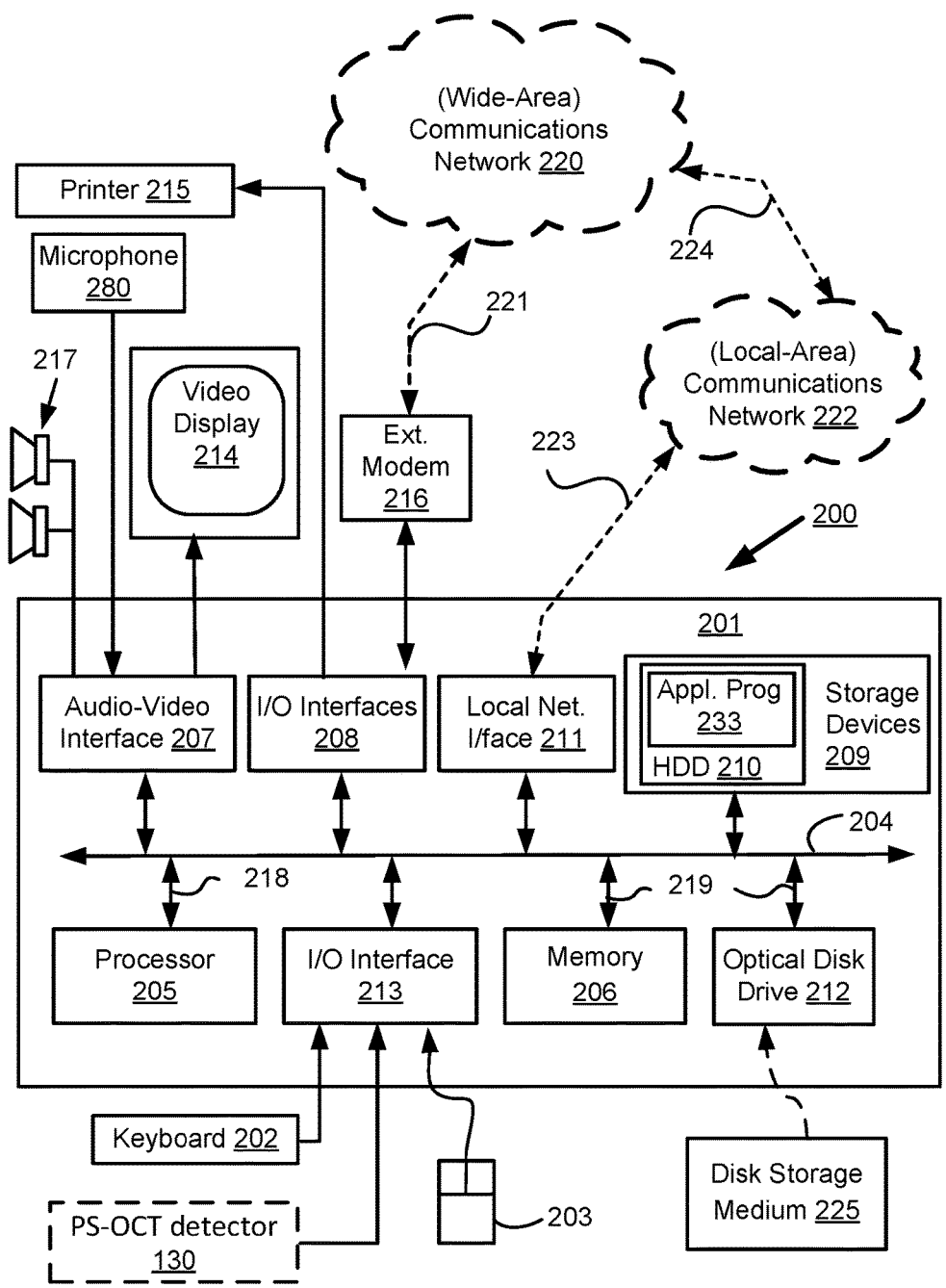
FIGS. 2A and 2B collectively form a schematic block diagram of a general purpose computer on which the described arrangements may be practised.
Figure 2B:
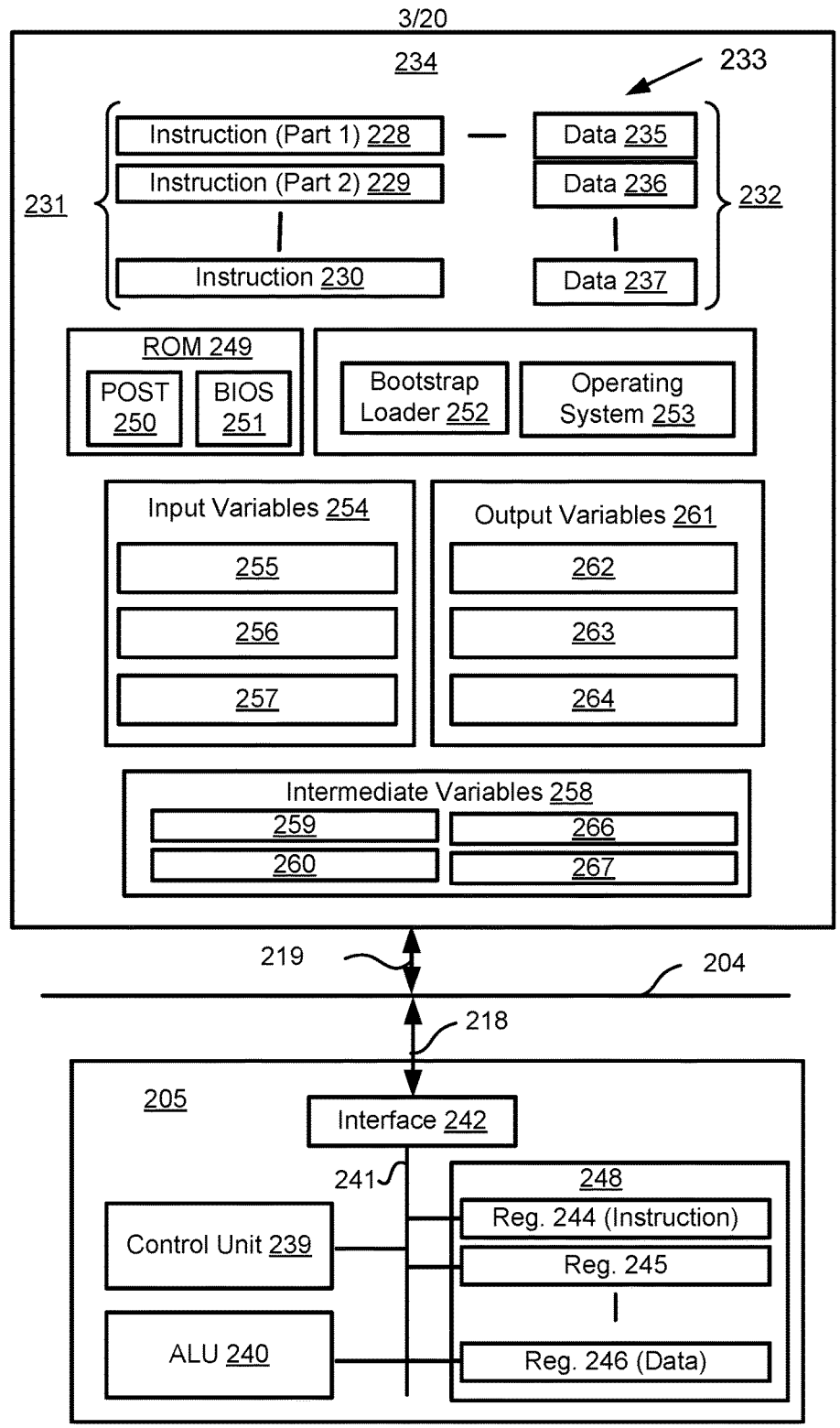

FIGS. 2A and 2B depict a general-purpose computer system 200, upon which the various arrangements described can be practiced, and which may be used to implement the functions of the computational unit 140, the storage unit 150 and the display unit 160.

As seen in FIG. 2A, the computer system 200 includes a computer module 201 representative of the computational unit 140, and input devices such as a keyboard 202, a mouse pointer device 203, and an input from the PS-OCT detector 130. The system 200 includes output devices including a printer 215, and a display device 214 (160), often supplemented by loudspeakers 217. An external Modulator-Demodulator (Modem) transceiver device 216 may be used by the computer module 201 for communicating to and from a communications network 220 via a connection 221. The communications network 220 may be a wide-area network (WAN), such as the Internet, a cellular telecommunications network, or a private WAN. Where the connection 221 is a telephone line, the modem 216 may be a traditional "dial-up" modem. Alternatively, where the connection 221 is a high capacity (e.g., cable) connection, the modem 216 may be a broadband modem. A wireless modem may also be used for wireless connection to the communications network 220.

The computer module 201 typically includes at least one processor unit 205, and a memory unit 206. For example, the memory unit 206 may have semiconductor random access memory (RAM) and semiconductor read only memory (ROM). The computer module 201 also includes an number of input/output (I/O) interfaces including: an audio-video interface 207 that couples to the video display 214, and loudspeakers 217; an I/O interface 213 that couples to the keyboard 202, mouse 203 or other human interface device (not illustrated), sand the PS-OCT detector 130. An interface 208 is also provided to couple with the external modem 216 and printer 215. In some implementations, the modem 216 may be incorporated within the computer module 201, for example within the interface 208. The computer module 201 also has a local network interface 211, which permits coupling of the computer system 200 via a connection 223 to a local-area communications network 222, known as a Local Area Network (LAN). As illustrated in FIG. 2A, the local communications network 222 may also couple to the wide network 220 via a connection 224, which would typically include a so-called "firewall" device or device of similar functionality. The local network interface 211 may comprise an Ethernet circuit card, a Bluetooth™ wireless arrangement or an IEEE 802.11 wireless arrangement; however, numerous other types of interfaces may be practiced for the interface 211.

The I/O interfaces 208 and 213 may afford either or both of serial and parallel connectivity, the former typically being implemented according to the Universal Serial Bus (USB) standards and having corresponding USB connectors (not illustrated). Storage devices 209 are provided and typically include a hard disk drive (HDD) 210. Other storage devices such as a floppy disk drive and a magnetic tape drive (not illustrated) may also be used. An optical disk drive 212 is typically provided to act as a non-volatile source of data. Portable memory devices, such optical disks (e.g., CD-ROM, DVD, Blu ray Disc™), USB-RAM, portable, external hard drives, and floppy disks, for example, may be used as appropriate sources of data to the system 200. The HDD 210 typically operates in concert with the processor 205 to functionally represent the storage unit 150 of FIG. 1 discussed above.

The components 205 to 213 of the computer module 201 typically communicate via an interconnected bus 204 and in a manner that results in a conventional mode of operation of the computer system 200 known to those in the relevant art. For example, the processor 205 is coupled to the system bus 204 using a connection 218. Likewise, the memory 206 and optical disk drive 212 are coupled to the system bus 204 by connections 219. Examples of computers on which the described arrangements can be practised include IBM-PC's and compatibles, Sun Sparcstations, Apple Mac™ or a like computer systems.

The methods of analysing tissues of a retina described herein may be implemented using the computer system 200 wherein the processes of FIGS. 3 to 19B, to be described, may be implemented as one or more software application programs 233 executable within the computer system 200. In particular, the steps of the methods of tissue analysis are effected by instructions 231 (see FIG. 2B) in the software 233 that are carried out within the computer system 200. The software instructions 231 may be formed as one or more code modules, each for performing one or more particular tasks. The software may also be divided into two separate parts, in which a first part and the corresponding code modules performs the tissue analysis methods, and a second part and the corresponding code modules may be used manage a user interface between the first part and the user.

The software may be stored in a computer readable storage medium, including the storage devices described below, for example. The software is loaded into the computer system 200 from the computer readable medium, and then executed by the computer system 200. A computer readable medium having such software or computer program recorded on the computer readable medium is a computer program product. The use of the computer program product in the computer system 200 preferably effects an advantageous apparatus for analysing the tissues of a retina.

The software 233 is typically stored in the HDD 210 or the memory 206. The software is loaded into the computer system 200 from a computer readable medium, and executed by the computer system 200. Thus, for example, the software 233 may be stored on an optically readable disk storage medium (e.g., CD-ROM) 225 that is read by the optical disk drive 212. A computer readable medium having such software or computer program recorded on it is a computer program product. The use of the computer program product in the computer system 200 preferably effects an apparatus for analysing tissues of a retina.

In some instances, the application programs 233 may be supplied to the user encoded on one or more CD-ROMs 225 and read via the corresponding drive 212, or alternatively may be read by the user from the networks 220 or 222. Still further, the software can also be loaded into the computer system 200 from other computer readable media. Computer readable storage media refers to any non-transitory tangible storage medium that provides recorded instructions and/or data to the computer system 200 for execution and/or processing. Examples of such storage media include floppy disks, magnetic tape, CD-ROM, DVD, Blu-ray Disc™, a hard disk drive, a ROM or integrated circuit, USB memory, a magneto-optical disk, or a computer readable card such as a PCMCIA card and the like, whether or not such devices are internal or external of the computer module 201. Examples of transitory or non-tangible computer readable transmission media that may also participate in the provision of software, application programs, instructions and/or data to the computer module 201 include radio or infra-red transmission channels as well as a network connection to another computer or networked device, and the Internet or Intranets including e-mail transmissions and information recorded on Websites and the like.

The second part of the application programs 233 and the corresponding code modules mentioned above may be executed to implement one or more graphical user interfaces (GUIs) to be rendered or otherwise represented upon the display 214. Through manipulation of typically the keyboard 202 and the mouse 203, a user of the computer system 200 and the application may manipulate the interface in a functionally adaptable manner to provide controlling commands and/or input to the applications associated with the GUI(s). Other forms of functionally adaptable user interfaces may also be implemented, such as an audio interface utilizing speech prompts output via the loudspeakers 217 and user voice commands input via the microphone 280.

FIG. 2B is a detailed schematic block diagram of the processor 205 and a "memory" 234. The memory 234 represents a logical aggregation of all the memory modules (including the HDD 209 and semiconductor memory 206) that can be accessed by the computer module 201 in FIG. 2A.

When the computer module 201 is initially powered up, a power-on self-test (POST) program 250 executes. The POST program 250 is typically stored in a ROM 249 of the semiconductor memory 206 of FIG. 2A. A hardware device such as the ROM 249 storing software is sometimes referred to as firmware. The POST program 250 examines hardware within the computer module 201 to ensure proper functioning and typically checks the processor 205, the memory 234 (209, 206), and a basic input-output systems software (BIOS) module 251, also typically stored in the ROM 249, for correct operation. Once the POST program 250 has run successfully, the BIOS 251 activates the hard disk drive 210 of FIG. 2A. Activation of the hard disk drive 210 causes a bootstrap loader program 252 that is resident on the hard disk drive 210 to execute via the processor 205. This loads an operating system 253 into the RAM memory 206, upon which the operating system 253 commences operation. The operating system 253 is a system level application, executable by the processor 205, to fulfil various high level functions, including processor management, memory management, device management, storage management, software application interface, and generic user interface.

The operating system 253 manages the memory 234 (209, 206) to ensure that each process or application running on the computer module 201 has sufficient memory in which to execute without colliding with memory allocated to another process. Furthermore, the different types of memory available in the system 200 of FIG. 2A must be used properly so that each process can run effectively. Accordingly, the aggregated memory 234 is not intended to illustrate how particular segments of memory are allocated (unless otherwise stated), but rather to provide a general view of the memory accessible by the computer system 200 and how such is used.

As shown in FIG. 2B, the processor 205 includes a number of functional modules including a control unit 239, an arithmetic logic unit (ALU) 240, and a local or internal memory 248, sometimes called a cache memory. The cache memory 248 typically includes a number of storage registers 244-246 in a register section. One or more internal busses 241 functionally interconnect these functional modules. The processor 205 typically also has one or more interfaces 242 for communicating with external devices via the system bus 204, using a connection 218. The memory 234 is coupled to the bus 204 using a connection 219.

The application program 233 includes a sequence of instructions 231 that may include conditional branch and loop instructions. The program 233 may also include data 232 which is used in execution of the program 233. The instructions 231 and the data 232 are stored in memory locations 228, 229, 230 and 235, 236, 237, respectively. Depending upon the relative size of the instructions 231 and the memory locations 228-230, a particular instruction may be stored in a single memory location as depicted by the instruction shown in the memory location 230. Alternately, an instruction may be segmented into a number of parts each of which is stored in a separate memory location, as depicted by the instruction segments shown in the memory locations 228 and 229.

In general, the processor 205 is given a set of instructions which are executed therein. The processor 205 waits for a subsequent input, to which the processor 205 reacts to by executing another set of instructions. Each input may be provided from one or more of a number of sources, including data generated by one or more of the input devices 202, 203, data received from an external source across one of the networks 220, 222, data retrieved from one of the storage devices 206, 209 or data retrieved from a storage medium 225 inserted into the corresponding reader 212, all depicted in FIG. 2A. The execution of a set of the instructions may in some cases result in output of data. Execution may also involve storing data or variables to the memory 234.

The disclosed retinal analysis arrangements use input variables 254, which are stored in the memory 234 in corresponding memory locations 255, 256, 257. The retinal analysis arrangements produce output variables 261, which are stored in the memory 234 in corresponding memory locations 262, 263, 264. Intermediate variables 258 may be stored in memory locations 259, 260, 266 and 267.

Referring to the processor 205 of FIG. 2B, the registers 244, 245, 246, the arithmetic logic unit (ALU) 240, and the control unit 239 work together to perform sequences of micro-operations needed to perform "fetch, decode, and execute" cycles for every instruction in the instruction set making up the program 233. Each fetch, decode, and execute cycle comprises:

(i) a fetch operation, which fetches or reads an instruction 231 from a memory location 228, 229, 230;

(ii) a decode operation in which the control unit 239 determines which instruction has been fetched; and (iii) an execute operation in which the control unit 239 and/or the ALU 240 execute the instruction.

Thereafter, a further fetch, decode, and execute cycle for the next instruction may be executed. Similarly, a store cycle may be performed by which the control unit 239 stores or writes a value to a memory location 232.

Each step or sub-process in the processes of FIGS. 3 to 19B is associated with one or more segments of the program 233 and is performed by the register section 244, 245, 246, the ALU 240, and the control unit 239 in the processor 205 working together to perform the fetch, decode, and execute cycles for every instruction in the instruction set for the noted segments of the program 233.

Figure 3A:
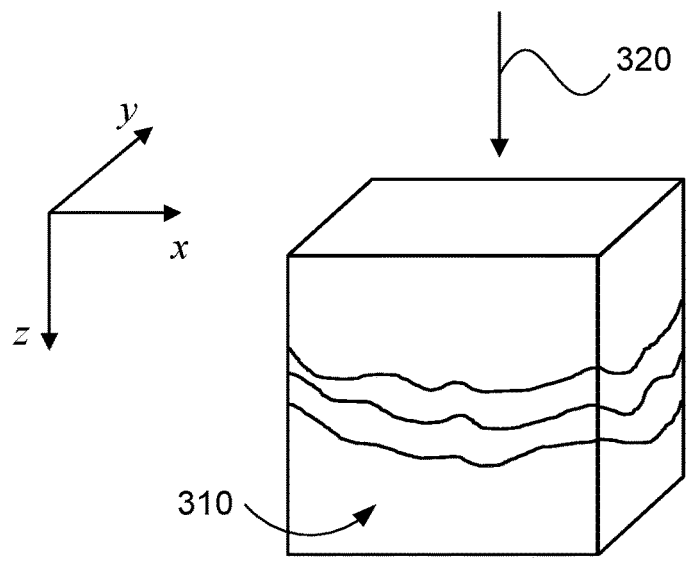
FIG. 3A shows an example of three-dimensional PS-OCT data of an eye.
Figure 3B:
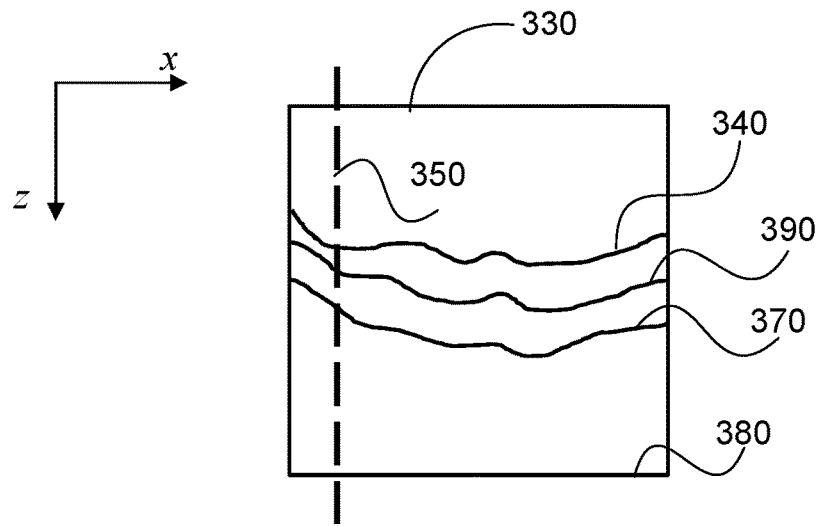
FIG. 3B shows an example of a B-scan from PS-OCT data of an eye.
Figure 3C:
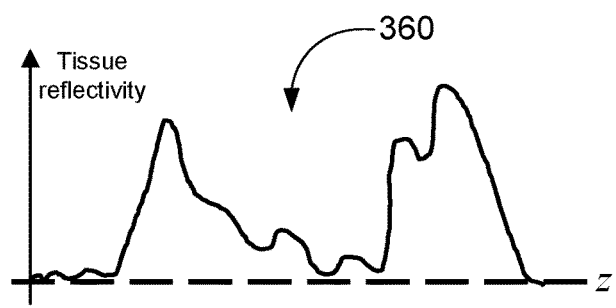
FIG. 3C shows an example of an A-scan corresponding to the indicated line in the B-scan of FIG. 3B.

FIGS. 3A to 3C show an example of acquired 3D reflectivity data by the OCT system of FIG. 1. In FIG. 3A, the volume (310) indicates the 3D OCT data formed from the detected and processed signals backscattered from the retina (126), where the arrow (320) indicates the direction of the incident scanning beam (114) in the space of the acquired OCT data. FIG. 3B shows a corresponding 2D B-scan (330) in a single X-Z plane from the 3D OCT data (310). The dashed line (350) represents the data captured in a single A-scan, and the graph of FIG. 3C shows an example of an A-scan signal (360). The curves shown in B-scan (330) indicate some relevant layers in the B-scan. The layers in the retina are differentiated by changes in the reflectivity of the layers which correspond to changes in the A-scan signal (360). For example, in FIG. 3B the curve (340) can be the inner limiting membrane (ILM), the curve (390) can be the photoreceptors above the RPE and the curve (370) can be the RPE layer. In the following description, the coordinate system shown in FIGS. 3A to 3C will be used to explain the physical relationship between tissues layers and orientations unless indicated otherwise.

Figure 4:
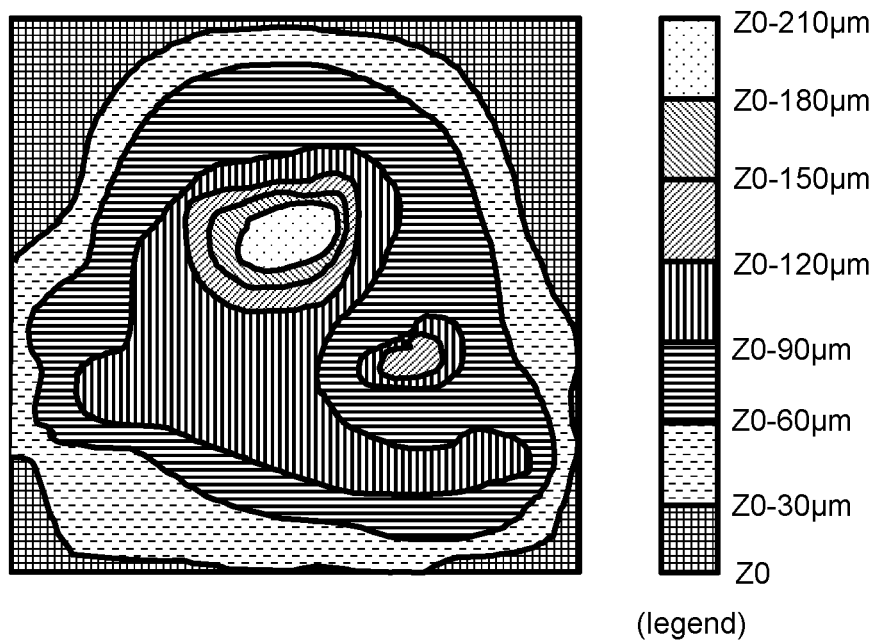
FIG. 4 is a contour plot of the 3D data described in FIG. 3A.

FIG. 4 demonstrates a contour representation of the 3D OCT data as viewed from the direction of the incident scanning beam (320). The contour plot in FIG. 4 represents the distance from the ILM to a constant depth $Z_0$. In the present description, $Z_0$ is taken to be the lowest Z location (380) in the B-scan (330).

Three-dimensional data collected from a PS-OCT system (100) have similar spatial structure as the 3D OCT data described above. However, the PS-OCT data (135) includes information on the polarization reflectivity properties of the tissue in addition to the intensity reflectivity properties that are measured by an OCT system. For each B-scan, the PS-OCT system (100) produces two complex polarization channel images $A_1(x,y)$ and $A_2(x,y)$ from the two orthogonal polarizations. These two polarization channel images are then used to calculate the polarization and intensity information in the form of four unnormalised Stokes parameters for each image pixel of the 2D B-scan. The unnormalised Stokes parameters are (i) the reflected wave intensity I, (ii) the horizontal and vertical linear polarization $\tilde{Q}$, (iii) the linear polarization at ±45 degrees $\tilde{U}$, and (iv) the circular polarization state, $\tilde{V}$. The unnormalised Stokes parameters are calculated from the polarization channel images $A_1(x,y)$ and $A_2(x,y)$—where each complex image is defined in terms of $A_1(x,y)=B_1 \exp(i\phi_1)$ and $A_2(x,y)=B_2 \exp(i\phi_2)$, where $B_1$ and $B_2$ are the magnitude and $\phi_1$ and $\phi_2$ are the phases of the polarization channel images—using the following equations:

$$I(x,y) = B_1^2 + B_2^2,$$

$$\tilde{Q}(x,y) = B_1^2 - B_2^2,$$

$$\tilde{U}(x,y) = 2B_1 B_2 \cos(\phi_1 - \phi_2),$$

$$\tilde{V}(x,y) = 2B_1 B_2 \sin(\phi_1 - \phi_2). \quad (1)$$

Normalized Stokes parameters are calculated by dividing the unnormalised Stokes parameters of Equation (1) by the intensity, I, as given in the following equations:

$$Q(x, y) = \frac{\tilde{Q}(x, y)}{I(x, y)},$$

$$U(x, y) = \frac{\tilde{U}(x, y)}{I(x, y)},$$

$$V(x, y) = \frac{\tilde{V}(x, y)}{I(x, y)}. \quad (2)$$

where the values of Q, U and V thus range from −1 to 1.

Figure 12:
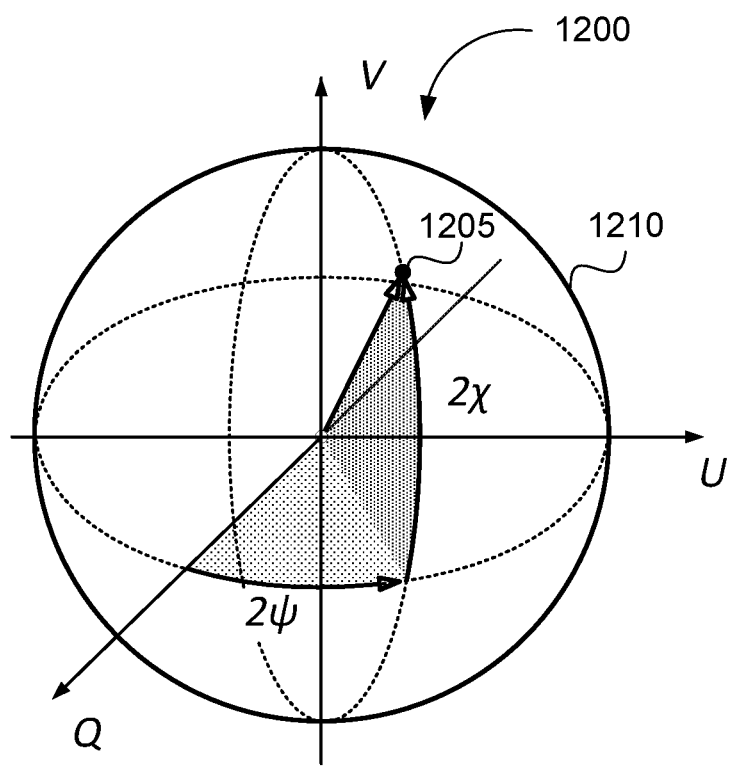
FIG. 12 is a graph showing the relationship of the normalized Stokes parameters to spherical coordinates on the unit sphere.

The Stokes parameters are related to the spherical coordinates of a point on the unit sphere defined by the values of the normalized stokes parameters, (Q,U,V), as illustrated in FIG. 12. The graph (1200) shows a point (1205) on the unit sphere (1210) whose position is defined by the elliptical angle, $\chi$, and the ellipticity of the polarization, $\psi$. The Stokes parameters are defined by these two angles according to the following equations:

$$Q(x,y) = \cos 2\psi \cos 2\chi,$$

$$U(x,y) = \sin 2\psi \cos 2\chi,$$

$$V(x,y) = \sin 2\chi. \quad (3)$$

From the normalized Stokes parameters of Equation (2), a degree of polarization uniformity (DOPU) value may be calculated using the equation:

$$DOPU(x,y) = \sqrt{Q_m^2(x,y) + U_m^2(x,y) + V_m^2(x,y)}, \quad (4)$$

where $Q_m$, $U_m$ and $V_m$ are spatially averaged normalized Stokes parameters calculated by averaging the respective values of the Stokes parameters using a sliding window, represented by the set of pixel offsets W. A typical sliding window size is 15-by-6 pixels. The DOPU value calculated using Equation (4) ranges from 0 to 1, where a DOPU value of 0 indicates completely depolarized light and a value of 1 indicates completely polarized light.

The values of the spatially averaged normalized Stokes parameters are additionally weighted by a mask, M(x,y), which is equal to one when the intensity at location (x,y) is greater or equal to than a threshold intensity and is equal to zero when the intensity is lower than this threshold. The mask allows the DOPU value to be less affected by pixels of low intensity, which may have highly noisy polarization directions.

The equations for the spatially averaged normalised Stokes parameters are as follows:

$$Q_m(x, y) = \frac{1}{N(x, y)} \sum_{(j,k) \in W} Q(x+j, y+k) M(x+j, y+k), \quad (5)$$

$$U_m(x, y) = \frac{1}{N(x, y)} \sum_{(j,k) \in W} U(x+j, y+k) M(x+j, y+k),$$

$$V_m(x, y) = \frac{1}{N(x, y)} \sum_{(j,k) \in W} V(x+j, y+k) M(x+j, y+k).$$

The factor N(x,y) is a normalisation factor for location (x,y). The normalization factor is equal to the sum of the mask values in the window by using the equation:

$$N(x, y) = \sum_{(j,k) \in W} M(x+j, y+k). \quad (6)$$

The DOPU value calculated using Equation (4) may be used to form an image with the same dimension as the polarization channel images $A_1(x,y)$ and $A_2(x,y)$. When the normalization factor is below a certain threshold, the DOPU value is set to a mask value, indicating the DOPU value is undefined at this location.

It has been observed that in the human eye RPE has a high reflectivity and also depolarizes the input light. Due to these properties, RPE tissue can be identified in a PS-OCT B-scan by detecting both high reflectivity and low DOPU value pixels, where the DOPU value is calculated using the method described above.

Figure 5A:
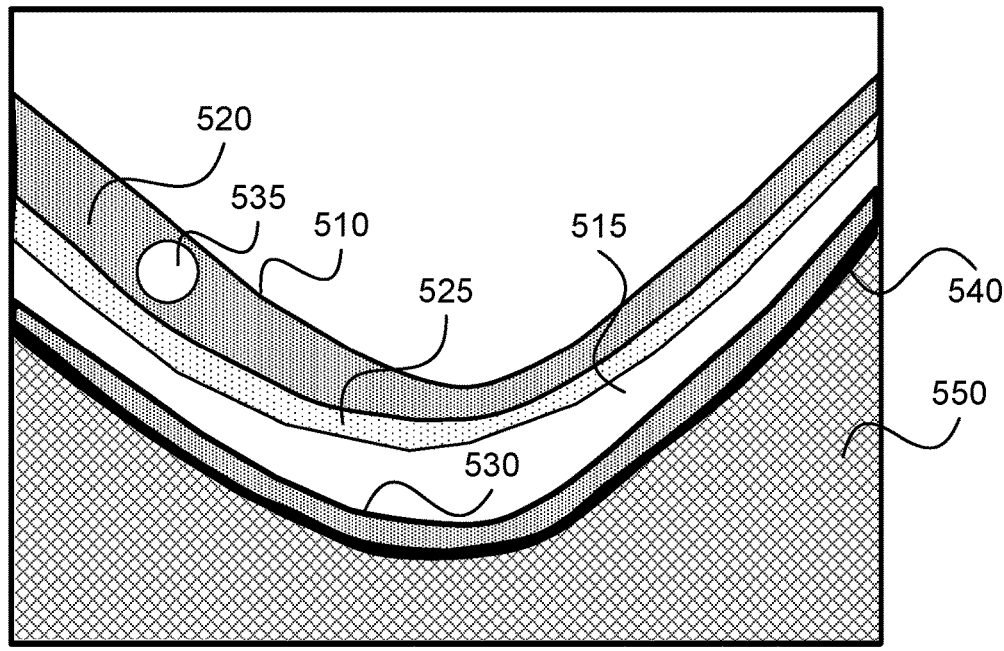
FIG. 5A shows an example cross section through the retina.

FIG. 5A illustrates an example cross-section of a retina. This diagram shows some important structures in the retina, including the inner limiting membrane (ILM) (510), the upper retinal layers including the retinal nerve fiber layer (RNFL) and ganglion cell layer (GCL) (520), the outer plexiform layer (OPL) (525), the outer nuclear layer (ONL) (515), the outer limiting membrane (OLM) (530), a blood vessel (535), the RPE and Bruch's membrane (540), and the choroid (550) in the X-Z plane indicated in FIG. 3. In a healthy eye, the RPE is firmly attached to the Bruch's membrane, which is itself firmly attached to the choroid (550), as shown in FIG. 5A. In an actual OCT or PS-OCT B-scan, because of the strong scattering effect of the RPE, Bruch's membrane and the choroid may not be clearly visible.

Figure 5B:
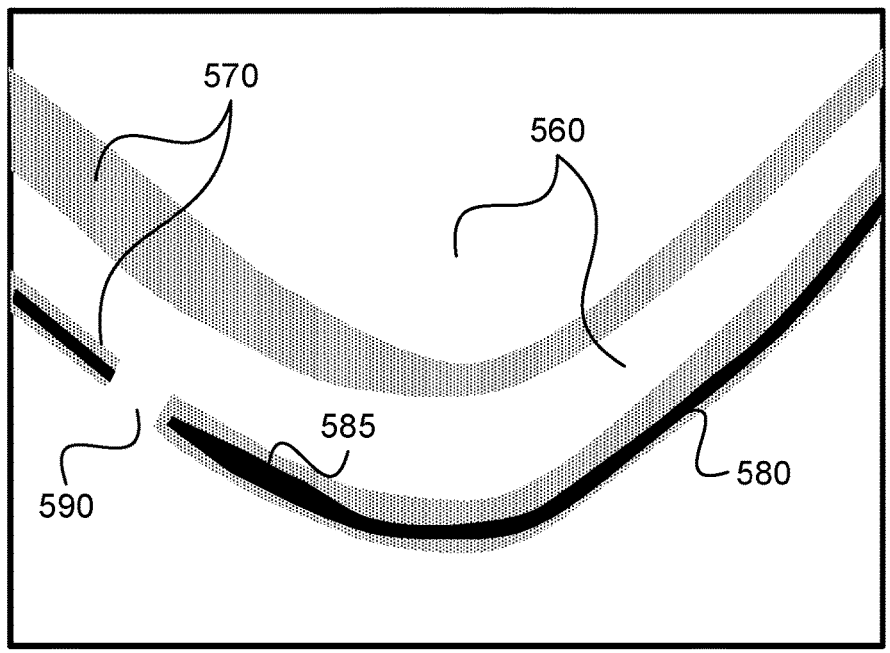
FIG. 5B shows an example of a processed PS-OCT B-scan with highlighted high back-scatter regions and retinal pigment epithelium (RPE)

FIG. 5B illustrates an example DOPU image from the same retinal cross-section as shown in Figure 5A. In this diagram, areas that have a low back-scattered intensity, for example the outer nuclear layer (ONL) (515) and above the ILM, may have DOPU values that are set to the mask value (560). Other areas that have high-intensity, such as the RPE (540) and the ganglion cell layer (GCL) (520), back-scattered signals may have DOPU values between 0 and 1, indicating the degree of depolarization of the back-scattered signal. In the case of the system (100) discussed here, low intensities correspond to intensity values below around 100 in arbitrary units, and high intensities above 1000 in arbitrary units corresponding to the units used in FIG. 14. For instance, the areas of the upper retinal layers (520) and other tissues which do not depolarize the signal are shown as having high DOPU values (570), whereas the RPE and other polarization scrambling tissues are shown as low DOPU values (580). Note that the structures can be different in the DOPU image from the intensity image due to the shadowing caused by absorption or scattering in areas above the structure of interest, as well as the polarization characteristics of different tissues. For example, the blood vessel (535) absorbs most of the incident light and causes structures below this to have low-intensity back-scattered signals. Therefore, the DOPU value may be the mask value in areas below blood vessels, as shown by an apparent gap in the RPE (590). Additionally, the thickness of the low-DOPU area corresponding to the RPE may change due to random polarization values that contribute to a low DOPU value (585).

Models of Random Polarization

The retina comprises polarization scrambling tissues, such as the RPE, which cause back-scattered light to be depolarized or, in other words, to have a randomized polarization. Additionally, a detected signal in the PS-OCT system (100) will contain noise. Therefore, in a real PS-OCT system with noise in the detected signal, there will be randomness in both the measured intensity and the polarization angle even for signals scattered from tissues that do not scramble the polarization.

As such, polarization randomness in PS-OCT measurements of structures in an eye originates from two different phenomena: a) polarization scrambling properties of some tissues in the retina, e.g. the RPE, and b) noise in the detected signal. Therefore, in order to accurately detect the RPE it is necessary to distinguish between the polarization randomness caused by noise and the polarization randomness caused by polarization scrambling.

PS-OCT Noise Model

In this section a noise model of the PS-OCT system is developed. Further, by assuming shot noise, additive noise, and multiplicative noise on the PS-OCT signal output (135) from the PS-OCT device (130), it is then possible to derive an approximate theoretical model of the randomness in the normalized Stokes parameters due to detection of noise in a polarized signal. This model of the randomness of the normalized Stokes parameters is called the directionally polarized distribution and is the probability distribution for the detected polarization for a back-scattered signal originating from polarization-maintaining tissue in the presence of detection noise. Using the derived directionally polarized distribution and a depolarized distribution of the expected randomness of a signal originating from polarization-scrambling tissue a Bayesian model of the relative likelihood of an area in the retina being polarization-scrambling (or depolarizing) is derived.

The main sources of noise in a PS-OCT device are shot noise in a photodetector array, and additive and multiplicative noise in the electronic components, of the PS-OCT detector (130). In the following, these three sources of noise are modelled as independent Gaussian distributed random processes. It is well known that the variance of shot noise is proportional to the output current of the photodetector, and the variance of multiplicative noise is proportional to the power of the signal. Therefore, the variance of noise in a signal containing all three noise sources is well approximated by the following formula:

$$\sigma_T^2 = S^2 \alpha_m^2 + S \alpha_s^2 + \sigma_a^2, \tag{7}$$

where S is the amplitude of the signal, $\alpha_m$ is a coefficient representing the strength of the multiplicative noise, $\alpha_s$ is a coefficient representing the strength of the shot noise, and $\sigma_a^2$ is the variance of the additive noise. Note that, the amplitude of the signal S in the noise model of Equation (7) is the amplitude of the signal before being transformed to the spatial domain using a discrete Fourier transform (DFT) by the computational unit (140).

Consider a simpler model of noise on the polarization signal in of the PS-OCT device that retains some elements of the expected noise behaviour. This simplified model of the randomness of the detected polarization is Gaussian identically distributed independent complex random noise in each of the two polarization channels $A_1$ and $A_2$ with a variance given by Equation (7), as given by the following formulae:

$$A_1 = a_1 + \frac{1}{2} n_1^{(r)} + \frac{i}{2} n_1^{(i)}, \tag{8}$$

$$A_2 = a_2 + \frac{1}{2} n_2^{(r)} + \frac{i}{2} n_2^{(i)},$$

where $n_k^{(r)} \sim N(0, \sigma_T^2)$ and $n_k^{(i)} \sim N(0, \sigma_T^2)$ are the noise in the real and imaginary components of the two polarization channels $A_1$ and $A_2$, and $N(\mu, \sigma^2)$ represents a Gaussian distribution with mean $\mu$ and variance $\sigma^2$.

Now consider unnormalized Stokes parameters calculated from the polarization channels of Equation (8) using Equation (1). Assuming the variance of the noise is much smaller than the signal, i.e. $\sigma_T^2 \ll I$, the noise on the unnormalized Stokes parameters may be approximated as Gaussian distributed with variance $\sigma_T^2$, as given by the following equations:

$$\tilde{Q} \sim N(\tilde{Q}_0, I \sigma_T^2), \tilde{U} \sim N(\tilde{U}_0, I \sigma_T^2), \tilde{V} \sim N(\tilde{V}_0, I \sigma_T^2), \tag{9}$$

where $\tilde{Q}_0$, $\tilde{U}_0$, and $\tilde{V}_0$ are the mean values of the distribution of Stokes parameters $\tilde{Q}$, $\tilde{U}$, and $\tilde{V}$ respectively.

The normalized polarization vector P is related to the unnormalized Stokes parameters by $IP = [\tilde{Q}, \tilde{U}, \tilde{V}]^T$ where the normalized polarization vector P is given by the following vector:

$$P = \begin{bmatrix} Q \\ U \\ V \end{bmatrix}, \tag{10}$$

and Q, U and V are Stokes parameters as given by Equation (2).

Introducing the dominant polarization direction which is defined with respect to the mean values of the Stokes parameter distributions of Equation (12) by the following equation:

$$\mu = \frac{1}{I_0} \begin{bmatrix} \tilde{Q}_0 \\ \tilde{U}_0 \\ \tilde{V}_0 \end{bmatrix}, \tag{11}$$

where the normalization parameter is defined so the dominant polarization direction has length one, thus $I_0 = \sqrt{\tilde{Q}_0^2 + \tilde{U}_0^2 + \tilde{V}_0^2}$. The distribution of the normalized polarization of Equation (10) can be derived using Equations (9) and (11) to obtain the following equation:

$$f_P(P) = C_P \exp\left(-\frac{1}{2I\sigma_T^2}[IP - I_0\mu]^T [IP - I_0\mu]\right), \tag{12}$$

where $C_p$ is a normalization factor. Equation (12) may be simplified by making the approximation that the noise is small with respect to the signal, so that $I \cong I_0$ for $\sigma_T \ll I$, to obtain the approximate distribution for the polarization vector of Equation (10) given by the following equation:

$$f_P(P) = C'_p \exp\left(\frac{I}{\sigma_T^2} \mu^T P\right), \tag{13}$$

where $C'_p$ is a normalization factor.

The directionally polarized distribution of Equation (13) is a von Mises-Fisher distribution for points on a unit sphere and represents the distribution of polarization that is expected for a polarized signal with detection noise. The standard form for the probability density function (PDF) for a von-Mises Fisher distributed polarization vector P is defined by two parameters: (i) a dominant polarization direction $\mu$ and (ii) a concentration $\kappa$ as given by the following equation:

$$f_D(P) = C(\kappa) \exp(\kappa \mu^T P), \tag{14}$$

where the vectors P and $\mu$ lie on the unit sphere such that $\|P\|=1$ and $\|\mu\|=1$. The concentration $\kappa$ operates as a control parameter of a predetermined probability density distribution function, namely the von-Mises Fisher distribution. Equation (14) is equivalent to the Equation (13) where the concentration parameter is related to the variance of Equation (7) and the intensity I of Equation (1) by the following equation:

$$\kappa = \frac{I}{\sigma_T^2} = \frac{I}{S^2 \alpha_m^2 + S \alpha_s^2 + \sigma_a^2}. \tag{15}$$

The factor C in Equation (14) is a normalisation coefficient and the normalization coefficient C depends only on the concentration parameter $\kappa$ and is calculated using the equation:

$$C(\kappa) = \frac{\kappa}{2\pi[\exp(\kappa) - \exp(-\kappa)]}. \tag{16}$$

Figure 6A:
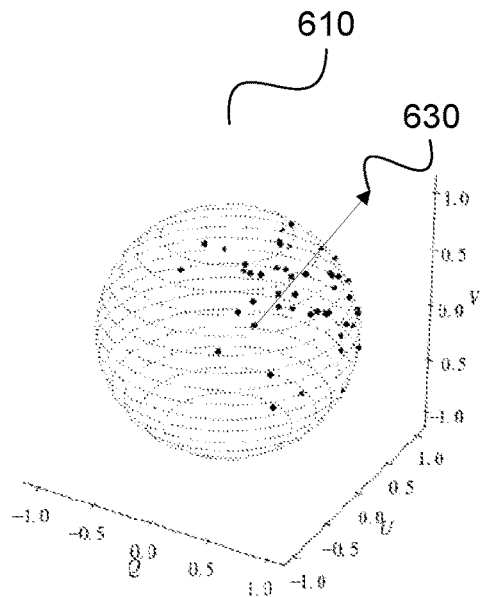
FIGS. 6A and 6B show examples of points on the unit sphere sampled from a von-Mises Fisher distribution with different concentration parameters.
Figure 6B:
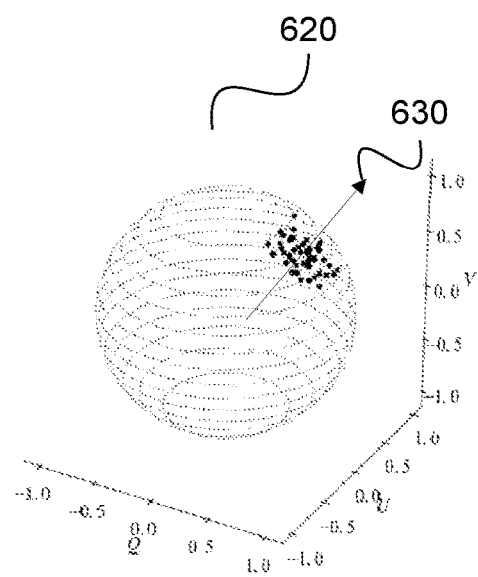

FIGS. 6A and 6B show two examples where 50 points are sampled from a three-dimensional von-Mises Fisher distribution defined by Equation (14) and each example is displayed along with a unit sphere. The first example (610) of FIG. 6A shows 50 points on the unit sphere sampled from a von-Mises Fisher distribution with a dominant polarization direction indicated by an arrow (630) and a concentration parameter of $\kappa=5$, which gives a large spread and the points are well separated. The second example (620) of FIG. 6B shows 50 points on the unit sphere sampled from a von-Mises Fisher distribution with a dominant polarization direction indicated by an arrow (630) and a concentration parameter of $\kappa=50$, which gives a small spread and the points are highly clustered around the dominant polarization direction.

Second, a model for polarization randomness caused by scattering from polarization scrambling tissue is proposed. The probability distribution of the polarization of a signal that is scattered from polarization scrambling tissue is termed the depolarized distribution. The simplest model for this depolarized distribution is a uniform distribution over all polarization directions. The probability density function (PDF) for a uniformly distributed polarization P is given by the equation:

$$f_U(P) = \frac{1}{4\pi}, \tag{17}$$

where the vector P lies on the unit sphere such that $\|P\|=1$.

Figure 6C:
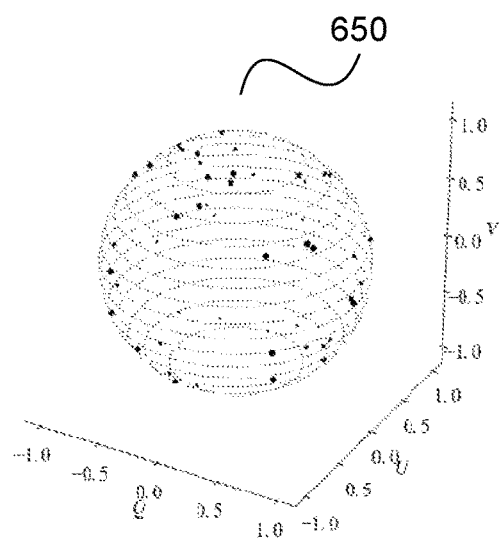
FIG. 6C shows an example of points on the unit sphere sampled from a uniform distribution.

An example of 50 points sampled from a uniform probability distribution on the Poincaré sphere (650) is shown in FIG. 6C.

Estimation of von Mises-Fisher Distribution Parameter

For the purposes of explanation, consider data M containing N measurements of the polarization of a signal, $P_k$, where the measurements are independent and identically distributed (IID), thus $M = \{P_k : k \in [0, \ldots, N-1]\}$. Furthermore, consider that this signal is sampled from von Mises-Fisher distribution. From data M estimated values of the dominant polarization direction $\mu$ and the concentration $\kappa$ of the signal can be obtained using maximum-likelihood estimation (MLE). A log-likelihood function for the dominant polarization direction $\mu$ and the concentration of the signal $\kappa$ given the data M (where data M is drawn from the same Mises-Fisher distribution) is given by the following equation:

$$L(\mu, \kappa; M) = N \log C(\kappa) + \kappa \sum_{k=0}^{N-1} \mu^T P_k. \tag{18}$$

An estimate $\mu^*$ for the dominant polarization direction $\mu$ can be found by finding values for $\mu$ and $\kappa$ to maximize Equation (18), subject to the constraints that the concentration $\kappa$ is positive or zero, $\kappa \geq 0$, and the dominant polarization direction $\mu$ has length one, $\|\mu\|=1$. The result is a maximum-likelihood estimate for the dominant polarization direction, and is given by the following equation:

$$\mu^* = \frac{\sum_k P_k}{\left\|\sum_k P_k\right\|} \tag{19}$$

Similarly, a maximum-likelihood estimate $\kappa^*$ for the concentration $\kappa$ can be found by finding values for $\mu$ and $\kappa$ to maximize Equation (18) subject to the constraints that the concentration $\kappa$ is positive or zero, $\kappa \geq 0$, and the vector of the dominant polarization direction has length one, $\|\mu\|=1$. The maximum-likelihood estimate for the concentration for a three-dimensional von-Mises Fisher distribution is obtained by solving the following equation, which is usually solved approximately:

$$\frac{1}{\tanh \kappa^*} - \frac{1}{\kappa^*} = \frac{1}{N}\left\|\sum_{k=0}^{N-1} P_k\right\|. \tag{20}$$

A well-known approximation to the maximum-likelihood estimate κ* is given by the following equation:

$$\kappa^* \simeq \frac{\bar{R}(3-\bar{R}^2)}{1-\bar{R}^2}. \quad (21)$$

The average polarization length $\tilde{R}$ of Equation 21 is defined by the following formula:

$$\bar{R} = \frac{1}{N}\left\|\sum_{l=1}^{N} P_l\right\|. \quad (22)$$

A useful approach to refine the approximation of Equation (22) is derived by rearranging Equation (20) as the following equation:

$$\kappa^*_{new} = \left[\frac{1}{\tanh\kappa^*} - \bar{R}\right]^{-1}. \quad (23)$$

A new estimate for the concentration parameter $\kappa^*_{new}$ can be calculated by evaluating the right hand side of Equation (23) using the estimated concentration parameter κ* from Equation (22).

In the data set received from a PS-OCT system, the concentration of the distribution of polarization is dependent upon the intensity of the back-reflected signal. Therefore, now consider a data set M containing N measurements of the polarization of the signal, $M=\{P_k: k\in[0,\ldots,N-1]\}$ and an associated concentration parameter $\kappa_k$ for each sample k, to form a set $K=\{\kappa_k: k\in[0,\ldots,N-1]\}$. The log-likelihood function for the dominant polarization direction μ is given by the following equation:

$$L(\mu; M, K) = \sum_{k=0}^{N-1} \log C(\kappa_k) + \kappa_k \mu^T P_k. \quad (24)$$

Considering that data set M is sampled from von Mises-Fisher distribution and that the concentration parameters $\kappa_k$ are known, the maximum-likelihood estimate for the dominant polarization direction μ* for heteroscedastic data can be found by finding a value for μ to maximize Equation (24) subject to the constraints that the mean direction has length one, ∥μ∥=1. The maximum-likelihood estimate for the dominant polarization direction for heteroscedastic data is thus given by the following equation:

$$\mu^* = \frac{\sum_k \kappa_k P_k}{\left\|\sum_k \kappa_k P_k\right\|}. \quad (25)$$

Weighted Bayesian Estimate of Depolarization

The DOPU of Equation (4) was developed as a measure of the amount of depolarization in a signal. In the following, a depolarization score is described in a Bayesian framework: this Bayesian depolarization score is measure of the relative likelihood that a signal is sampled from a depolarized distribution (modelling a signal backscattered from polarization scattering tissue) versus a directionally polarized distribution (modelling a signal backscattered from polarization maintaining tissue) is introduced.

Consider that a signal of interest is either sampled from a directionally polarized distribution, having a single dominant polarization direction, or sampled from a depolarized distribution. A random variable Λ denotes that the signal of interest is sampled from the directionally polarized distribution, with a value Λ=1, or the depolarized distribution, with a value Λ=0. The ratio of a probability that a data point is drawn from the directionally polarized distribution, given polarization data $M=\{P_k: k\in[0,\ldots,N-1]\}$ and associated concentration $K=\{\kappa_k: k\in[0,\ldots,N-1]\}$, and a probability that the data point is drawn from the depolarized distribution, given the polarization data M, is referred to as the likelihood ratio for the directionally polarized distribution versus the depolarized distribution and given by R in the formula:

$$R = \frac{P(\Lambda=1|M,K,\mu)}{P(\Lambda=0|M)} = \frac{\int P(M,\mu|K,\Lambda=1)P(\mu)d\mu P(\Lambda=1)}{P(M|\Lambda=0)P(\Lambda=0)}, \quad (26)$$

where the probability P(Λ=1) represents the prior probability that the data comes from a directionally polarized distribution and the probability P(Λ=0) represents the prior probability that the data comes from a depolarized distribution. These prior probabilities can be estimated from data, approximated using domain knowledge, or both set to ½ as an uninformative prior In the likelihood ratio of Equation (26), the probability of the signal being polarized is given by the integral over all possible dominant polarization directions of the likelihood of the data given that dominant polarization direction. Equation (26) can be simplified by considering that the probability density function of the dominant polarization direction is concentrated near an estimated dominant polarization direction μ* as given by Equation (25). Taking a concentrated density as a Dirac delta function located at the estimated dominant polarization direction, μ*, the probability density function of the dominant polarization direction is given by the following equation:

$$P(\mu)=\delta(\mu-\mu^*). \quad (27)$$

Using the probability density function for the dominant polarization direction of Equation (27), the log-likelihood ratio of Equation (26) can be rewritten as the following equation:

$$D(M;K) = \sum_{k=0}^{N-1} f_D(P_k;\mu,\kappa_k) - \sum_{k=0}^{N-1} f_U(P_k) + \gamma, \quad (28)$$

where the constant γ is calculated from the ratio of prior probabilities by the following equation:

$$\gamma = \log\frac{P(\Lambda=1)}{P(\Lambda=0)}. \quad (29)$$

and where $f_D$ is a polarized (or directional) distribution (i.e., given Λ=1) and $f_U$ is a depolarized (or uniform) distribution (i.e., given Λ=0).

Furthermore, taking the probability density function for the directionally polarized distribution $f_D$ as the von-Mises-Fisher distribution of Equation (14) and the depolarized distribution $f_U$ as given by Equation (17), then the log-likelihood ratio is a score function which can be written as the following equation:

$$D(M; K) = \sum_{k=0}^{N-1} [\log C(\kappa_k) + \kappa_k \mu^* \cdot P_k] + N\log 4\pi + \gamma. \quad (30)$$

When the value of the score function of Equation (30) is greater than zero, the data is more likely to have been drawn from a von-Mises-Fisher distribution than a uniform distribution. If the directionally polarized distribution is considered to be a von-Mises-Fisher distribution and the depolarized distribution is considered to be a uniform distribution, then only the projection of the polarization data in the estimated dominant polarization direction $\mu^*$ is used to distinguish between data sampled from a directionally polarized distribution and depolarized distribution.

As the log-likelihood function of Equation (19) is additive, a weighted calculation can also be performed where each sample is weighted by weight $w_v$. The weights $w_0, \ldots, w_{N-1}$ may be scaled so that the weights sum to one, that is, so that $\Sigma_{k=0}^{N-1} w_v = 1$. Then a weighted depolarization score function is given by the following equation:

$$D(M; K) = \sum_{k=0}^{N-1} w_v[\log C(\kappa_k) + \kappa_k \mu^* \cdot P_k] + \log 4\pi + \gamma, \quad (31)$$

Equations (30) and (31) suffer from numerical overflow when evaluated directly using fixed precision arithmetic operations for large or small values of the concentration, $\kappa_k$. Therefore, it is better to evaluate the log of the normalization coefficient C of Equation (16) using an asymptotic formula. For a small value of the concentration, $\kappa \ll 1$, the log of the normalization coefficient C may be approximated as the following asymptotic formula which is valid as $\kappa$ approaches zero:

$$\log C(\kappa) \simeq -\log(4\pi) - \log\left(1 + \frac{\kappa^2}{6}\right) \quad (32)$$

For a large value of the concentration, $\kappa \gg 1$, the log of the normalization coefficient C may be expanded as a Taylor series around $1/\kappa=0$ which gives the following approximate formula:

$$\log C(\kappa) \simeq \log(\kappa) - \log(2\pi) - \kappa \quad (33)$$

Relationship of the Polarization Concentration to the Intensity

The noise in the polarization vector was shown to be approximately connected to the noise in the input polarization channel images $A_1$ and $A_2$ by Equation (15) and therefore to the noise in the PS-OCT device. The present inventors propose that the concentration can be approximated as a function of the signal intensity by replacing the PS-OCT squared signal amplitude $S^2$ before the DFT in Equation (7) with the signal intensity I defined in Equation (1).

$$\kappa(I) = \frac{I}{I\sigma_m^2 + I^{0.5}\sigma_s^2 + \sigma_a^2}, \quad (34)$$

As the distribution is assumed to represent the noise after the DFT, the noise variances $\sigma_m^2$, $\sigma_s^2$, and $\sigma_a^2$ may be unknown. In practice, Equation (34) may be fitted to data from a real PS-OCT system. The present inventors have found that a good fit to the empirical data is obtained by fitting the following simpler function, where only multiplicative and additive noise is modelled:

$$\kappa(I) = \frac{I}{\alpha_1 I + \alpha_0}, \quad (35)$$

However, when fitting a function such as Equation (35), it is desirable to ensure that the data contains only measurements that are sampled from a directional distribution. This is because PS-OCT data captured from polarization-scrambling regions can affect the empirically determined relationship between intensity I and concentration $\kappa$. This can be avoided by only using polarization measurements from regions that have values of the depolarization score of Equation (30) that are greater than a particular threshold, $D_{th}$. This is an iterative process: starting with reasonable initial values for the parameters $\alpha_0$ and $\alpha_1$ and threshold $D_{th}$, the likely depolarizing regions may be found. The relationship between intensity I and concentration $\kappa$ may then be determined empirically excluding data from the likely depolarizing regions, and new values for parameters $\alpha_0$ and $\alpha_1$ may be determined. In practice, this process typically requires a single iteration to give useful values for the parameters.

Figure 14A:
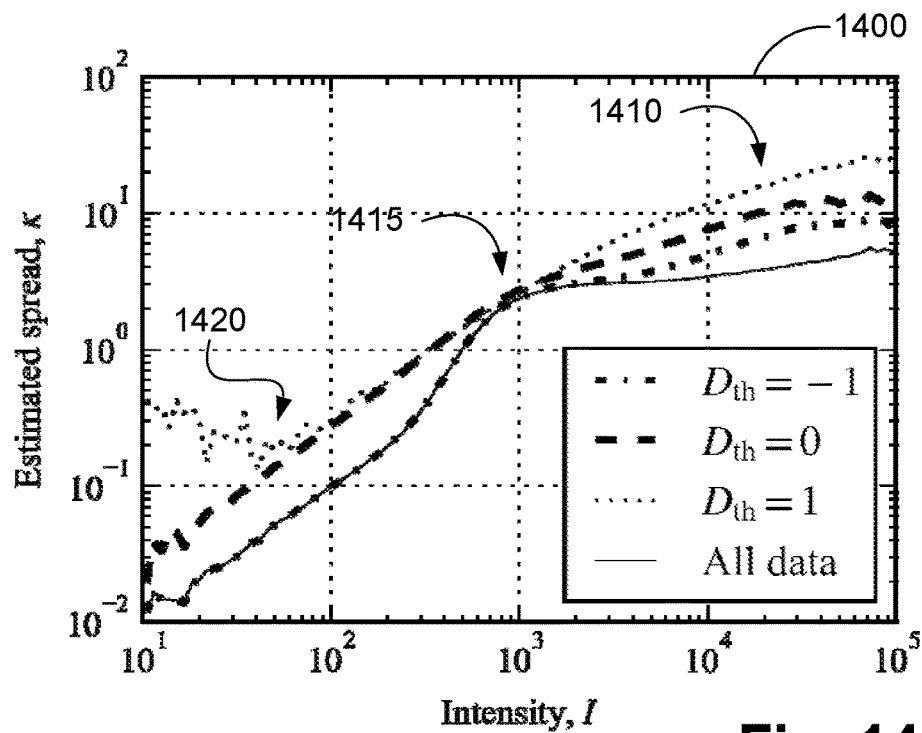
FIG. 14A is a graph showing the empirical relationship between the polarization concentration and the intensity from acquired PS-OCT data, as calculated in the method of FIG. 7.

FIG. 14A illustrates this effect. The graph (1400) of FIG. 14A shows the concentration $\kappa$ (i.e. estimated spread) versus the intensity I for three different values of a depolarization mask threshold $D_{th}$ and for the case where no data is masked. For the curve labelled "all data" no masking is performed, and there is a considerable deviation of the curve from the expected relationship of the concentration parameter to the intensity, in particular the "hump" (1415) near intensities below $10^3$ (in arbitrary units). When the depolarization mask threshold $D_{th}$ is set to zero (the expected threshold value between polarization-preserving and polarization-scrambling measurements) then a linear relationship is obtained for intensities below $10^3$ (in arbitrary units), as expected for small intensities from Equation (35). When the depolarization mask threshold $D_{th}$ is set to one, less data from polarization-scrambling regions are included and the relationship between concentration and intensity changes in the higher intensity region above $10^3$; however, as there are more data ignored in lower intensities the curve in the low intensity region (1420) deviates considerably from the expected linear relationship. Therefore, a reasonable threshold $D_{th}$ may be determined so that the both the low and high intensity regions contain sufficient number of samples and are not highly biased by signals from polarization-scrambling tissue; in the example of FIG. 14A, reasonable values are those between $D_{th}=0$ and $D_{th}=1$.

The parameter $\alpha_0$ models the slope in the low intensity region (1420) and the parameter $\alpha_1$ models the roll-off from the linear relationship in the high intensity region (1410). In practice, the values for both parameters may be computed simultaneously using a least-squared optimal fit of the functional relationship of Equation (35) to the concentration parameters determined from experimental data. An example of a least-squares parameter fit is given in FIG. 14B. The graph (1450) shows the data stored at step (760), to be described, for the concentration κ at each intensity and the optimal least-squares fit to the function of Equation (34) which is obtained with parameter values of $\alpha_1 = 4.6 \times 10^{-3}$ and $\alpha_0 = 7.1 \times 10^{-2}$.

Figure 7:
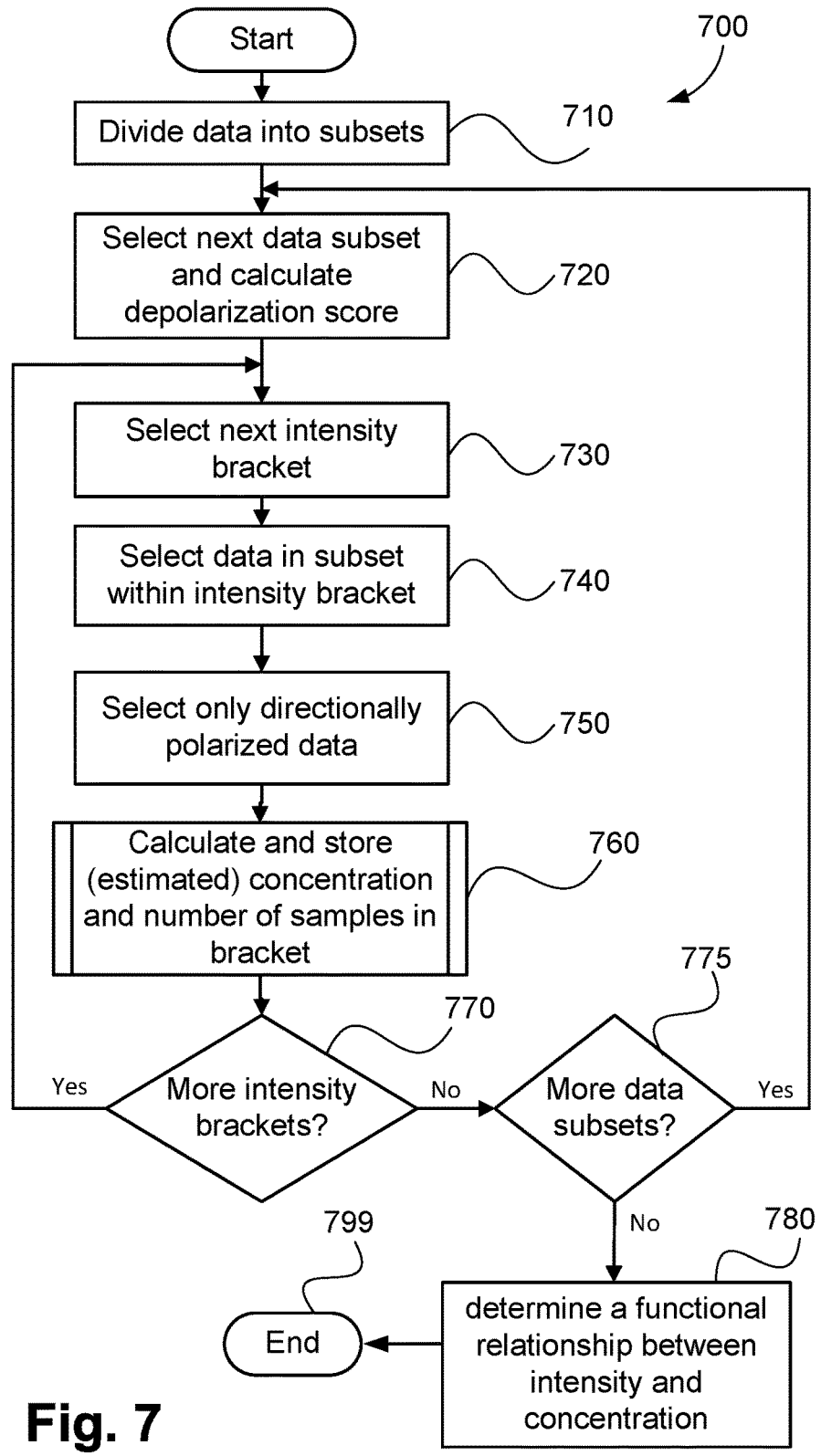
FIG. 7 is a schematic flow diagram illustrating a method of determining a relationship between concentration and intensity from acquired PS-OCT data.

First Implementation
Calculating the Concentration Versus Intensity Relationship The relationship between the expected concentration of polarization direction and the intensity can be determined theoretically or empirically from PS-OCT data captured by the system 100. The flow diagram of FIG. 7 shows a method for the calculation of the empirical concentration of polarization direction versus the intensity from a previously acquired PS-OCT data set, for example as stored in the storage 150 or HDD 210. The method (700) is preferably implemented in software, stored on the HDD (210) and executable by the processor (205) as part of the application (233) to calculate, according to the above, an estimate of concentration κ versus intensity I for selected intensity values.

The method (700) operates upon previously acquired PS-OCT data (135) including data elements given as a number of measurements of the intensity and polarization, as extracted from the HDD (210) by the processor (205). At step (710) the processor (205) divides the PS-OCT data set (135) into one or more subsets denoted $S_1, \ldots, S_K$ where K is the number of subsets. The subsets may be chosen to be individual B-scans of a previously acquired PS-OCT volume, or may be sub-volumes of the full 3D volume that is captured by the PS-OCT system (100). At step (710) a subset counter is initialized to the first subset, $k \leftarrow 1$.

At step (720) the (next) subset, $S_k$, is chosen for processing in steps (720)-(770) according to the subset counter. The chosen subset is formed of L samples of intensity and polarization, denoted by the set of L intensity measurements, $\{I_1, \ldots, I_L\}$, and the set of L polarization measurements, $\{P_1, \ldots, P_L\}$. A depolarization score, $D_l$, for all measurements $l \in [1 \ldots L]$ in the current subset is calculated in step (720) by the processor (250), which can be used later to mask only samples that likely come from a directionally polarized distribution. The calculation of a depolarization score as performed in step (720) can be preferably performed according to the method (900) of FIG. 9, or the method (1600) of FIG. 16. Alternatively, other techniques, such as DOPU, may be used.

Values for the estimated concentration κ* are also calculated by the processor (250) in step 720 using polarization measurements of approximately the same intensity. The calculation is performed by selecting monotonically increasing intensity intervals $[I_m, I_{m+1}]$, where $m \in \{1, 2, \ldots, M+1\}$ and M is the number of intensity intervals. Here an intensity interval counter is initialized to the first bracket, $m \leftarrow 1$.

At step (730) the (next) intensity interval is selected, $[I_m^{(B)}, I_{m+1}^{(B)}]$ according to the intensity interval counter. At step (740) the polarization measurements of the current data subset, $S_k$, that have corresponding intensities within the current intensity bracket are selected. The set of measurement indices, $T_k$, that are selected within the current data subset, $S_k$, are determined according to the following equation:

$$T_k = \{l \in [1 \ldots L] | I_m^{(B)} \leq I_l < I_{m+1}^{(B)}\} \quad (36)$$

At step (750) the measurements within the current intensity interval, as determined in step (740), are selected if the measurements are likely to come from polarization-preserving tissue. More specifically, the samples that may have been scattered from tissue that is polarization scrambling are removed. This results in the selection of only directionally polarized data. To remove measurements that likely come from polarization-scrambling tissue, a manual labelling of tissue or an automated selection technique may be used. For example, a threshold depolarization, $D_{th}$, can be used where the pixels above this threshold can be considered to have been backscattered from polarization-preserving tissue. The set of selected samples $T'_k$ are then given by the following equation:

$$T'_k = \{l \in T_k | D_l \geq D_{th}\}. \quad (37)$$

At step (760) an estimated value for the concentration is calculated by the processor (250) using the selected subset of data, $T'_k$. The calculation of the concentration is further detailed later with reference to FIG. 8. The estimate of the concentration and the number of samples in the set $T'_k$ calculated in step (760) are stored to be used in step (780), discussed below.

In step (770) the intensity interval counter, m, is tested to check if all intensity intervals have been computed, $m \geq M$. If there are more intervals to compute, the interval counter is incremented so that $m \leftarrow m+1$ and the process (700) returns to step (730). Otherwise control continues to step (775).

In step (775) the data subset counter, k, is compared to the number of subsets, K, to determine if all data subsets have been computed. If $k < K$, there are more subsets to compute, and the data subset counter is incremented, $k \leftarrow k+1$. The process (700) then returns to step (720). Otherwise, the method (700) continues to step (780).

Finally, in step (780) the concentration values and the number of samples in the set $T'_k$, as stored in step (760), are used to determine a functional relationship between intensity and concentration. The functional relationship between intensity and concentration can be parametric or non-parametric.

For a parametric relationship, the parameters $\alpha_1$ and $\alpha_0$ of Equation (35) may be found using a least-squares fit to the concentration values stored in step (760) and weighted by the weighting factor stored in step (760). For a non-parametric relationship, histograms associated with the intensity and concentration may be stored and used directly to determine the relationship between concentration and intensity.

The method (700) then terminates at step (799) returning the estimate of concentration κ versus intensity I for selected intensity values.

Calculating the Polarization Concentration

Figure 8:
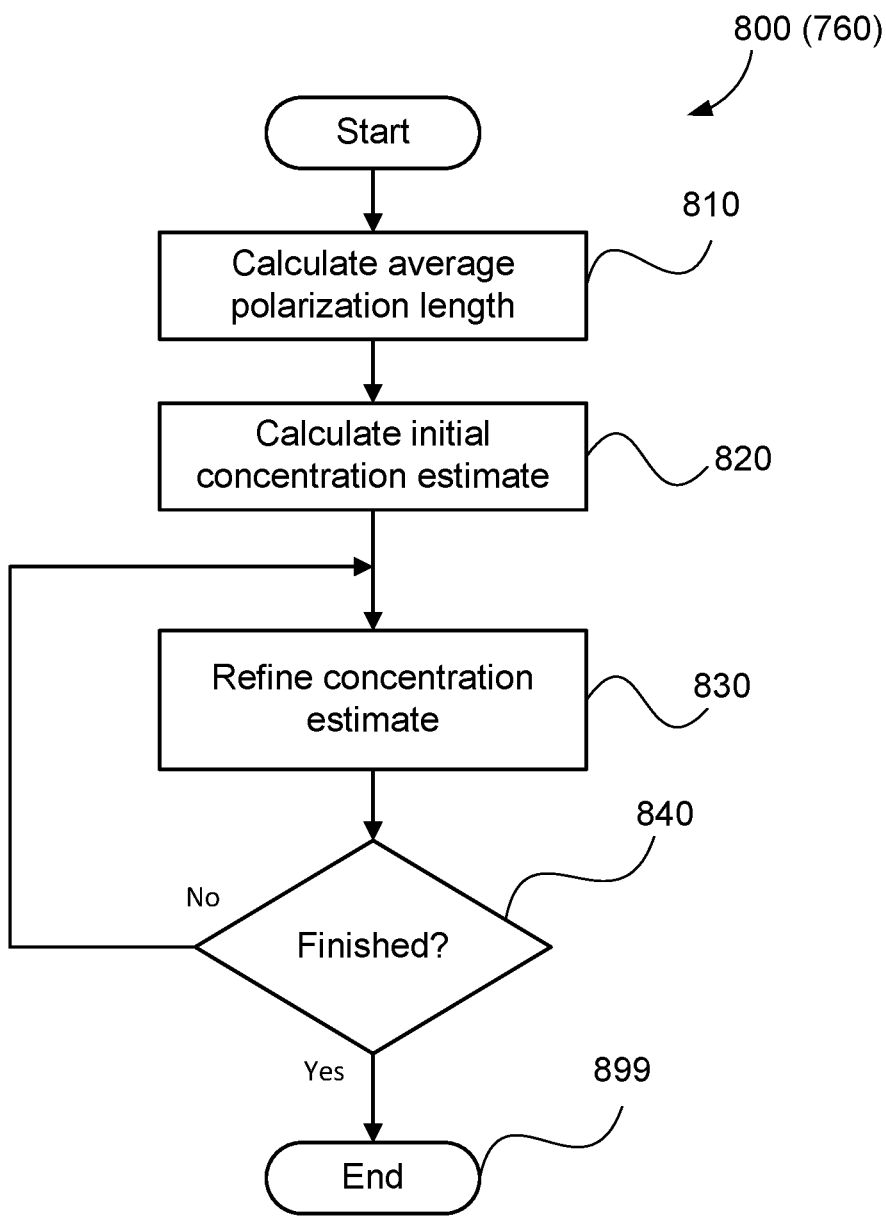
FIG. 8 is a schematic flow diagram illustrating a method of determining an estimate of the polarization concentration from polarization measurements.

A preferred implementation of step (760) will now be explained with reference to the method (800), shown in the flow diagram of FIG. 8. The method (800) operates initially upon previously acquired PS-OCT measurements provided as N measurements of the polarization represented as the vectors $P_l$, where $l \in \{1, 2, \ldots, N\}$. At step (810) an average polarization length $\bar{R}$ is calculated by the processor (250) by averaging all polarization vectors $P_l$ and calculating the length of the average vector using Equation (22). Then, at step (820) an initial estimation of the concentration is calculated by the processor (250) using Equation (21), as given in the following equation:

$$\kappa_1 \leftarrow \frac{\overline{R}(3-\overline{R}^2)}{1-\overline{R}^2}. \qquad (38)$$

A loop counter is then set to k←1 and the current estimate of the concentration $\kappa_1$ is saved, for example by storing in the memory 206, to be used in the following steps.

The initial estimate of the concentration is then refined by fixed-point iteration to solve Equation (20). At step (830) a refined estimate of the concentration is calculated by the processor (250) using Equation (23) and the current estimate of the concentration $\kappa_k$, as given by the following equation:

$$\kappa_{k+1} \leftarrow \left[\frac{1}{\tanh\kappa_k} - \overline{R}\right]^{-1}. \qquad (39)$$

At step (840) the convergence of the estimate is tested by comparing the current estimate from step (830) with the previous estimate as input to step (830). If the convergence meets a predetermined threshold given by the inequality $\|\kappa_{k+1}-\kappa_k\|<\epsilon$, or if the loop counter exceeds a predetermined loop count, the estimate is accepted and returned to the method (700) in step (899). Otherwise, the loop counter is incremented, k←k+1, and the method (800) returns from step (840) to step (830).

Calculating the Depolarization Score

Figure 9:
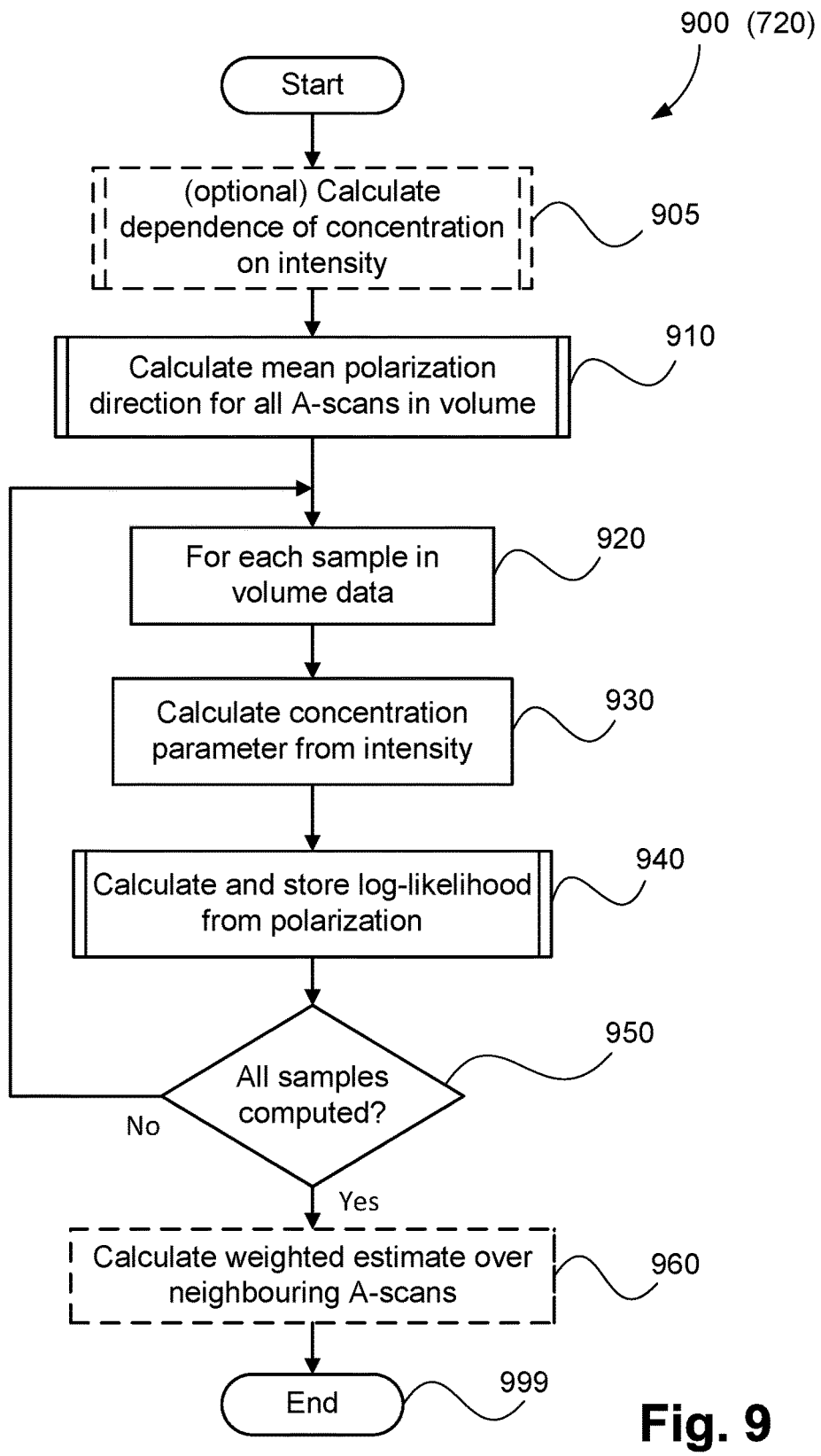
FIG. 9 is a schematic flow diagram illustrating a method for calculating a depolarization score from acquired PS-OCT data.

One approach to calculation of a depolarization score is now explained with reference to a method (900) shown in FIG. 9. The method (900) operates upon previously acquired PS-OCT measurements in a scan volume, where polarization measurements are represented as the vectors P(j,k,l), and intensity measurements are represented as the values I(j,k,l) where j∈{1, 2, . . . , $N_x$} indexes the x-direction, k∈{1, 2, . . . , $N_y$} indexes the y-direction, and l∈{1, 2, . . . , $N_z$} index the z-direction. Here the z-direction corresponds to the direction of an A-scan, the x-direction corresponds to the orthogonal direction used to capture a B-scan, and the y-direction corresponds to the direction used to capture successive B-scans, as illustrated in FIGS. 3A to 3C.

In an optional initial step (905), the concentration dependence on the intensity is calculated from the provided polarization and intensity measurements by the processor (250). Alternatively, a predetermined dependence of the concentration on the intensity is provided to the method (900), for example the dependence of Equation (35) where the values of parameters $\alpha_0$ and $\alpha_1$ are known. A method for determining the concentration dependence on the intensity, given previously acquired PS-OCT polarization and intensity measurements, is the method (700) of FIG. 7.

Figure 10:
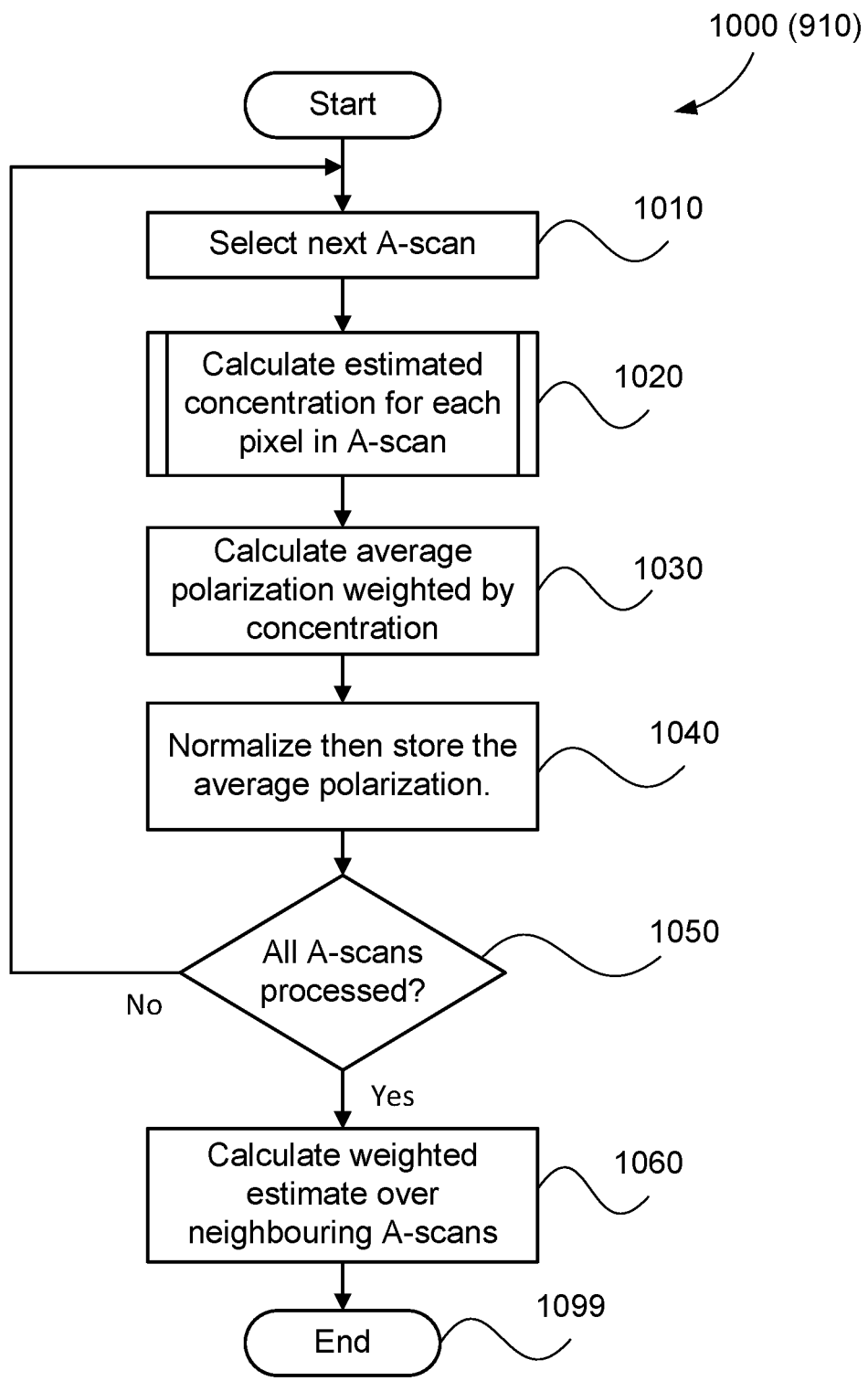
FIG. 10 is a schematic flow diagram illustrating a method of determining a dominant polarization direction from acquired PS-OCT data.

In step (910) the estimated dominant polarization direction, $\mu^*(j,k)$, is calculated by the processor (250) for all A-scans in the provided PS-OCT volume data, as detailed in the method of FIG. 10. At this point, the volume indices (j,k,l) are initialized to point to the first sample in the volume.

In step (920) the next sample from the volume data is selected, as specified by the indices (j,k,l). In the next step (930), the estimated concentration $\kappa^*(j,k,l)$ is calculated by the processor (250) for the current sample, using the intensity I(j,k,l) and a relationship between concentration and intensity, as previously calculated using the method of FIG. 7. A relationship between concentration and intensity for the current volume data may alternatively or additionally be calculated in optional step (905), or alternatively may be prior-determined from other volume data and provided to the method (900). For example, the other volume data can a volume data obtained from other patients examined by the same PS-OCT device. In particular, in the case of a parametric relationship the parameters $\alpha_0$ and $\alpha_1$ of Equation (35) estimated in the method of FIG. 7 are now used to calculate the estimated concentration using the following equation $$\kappa^*(j,k,l) \leftarrow \frac{I(j,k,l)}{\alpha_1 I(j,k,l) + \alpha_0}, \qquad (40)$$

The calculated concentration may be stored in memory, such as the RAM (206) or HDD (210) in association with the corresponding intensity values.

Next, in step (940) the depolarization score function of Equation (30) is calculated by the processor (250) using $\mu^*(j,k)$ and $\kappa^*(j,k,l)$ for the measurements with indices (j,k,l). The calculated depolarization score function is stored in a depolarization score array D(j,k,l), for example stored within the HDD 210. The calculation of the depolarization score function is detailed in the method of FIG. 11.

Next, in step (950), if there are more samples to be computed in the volume, the volume indices are incremented to point to the next sample, and the method (900) passes back to step (920). Otherwise, control continues to step (960).

Finally, optionally in step (960), an averaged, or linearly filtered, depolarization score $D_{av}(j,k,l)$ is calculated by the processor (250) from the depolarization scores D(j,k,l) stored in step (940), using a weighted average of the volume data over appropriate ranges of data in the x-direction, the y-direction, and the z-direction using the following equation:

$$D_{av}(j,k,l) \leftarrow \frac{1}{W} \sum_{t=-M_t}^{M_t} \sum_{u=-M_u}^{M_u} \sum_{v=-M_v}^{M_v} w(t,u,v) D(j+t, k+u, l+v), \qquad (41)$$

where the weighting normalization, W, is given by the following equation:

$$W = \sum_{t=-M_t}^{M_t} \sum_{u=-M_u}^{M_u} \sum_{v=-M_v}^{M_v} w(t,u,v). \qquad (42)$$

The weights w(t,u,v) may be, for example, a Gaussian weighting, as given by the following equation:

$$w(t,u,v) \leftarrow \exp[-(t^2+u^2+v^2)/(2\sigma_s^2)], \qquad (43)$$

where the width of the weighting function $\sigma_s$ is chosen so that the data is accumulated over a volume that is representative of the expected size of polarization-scrambling structures in the retina. Alternatively, different widths for each of the x-direction, the y-direction, and the z-direction can be used to give an asymmetric weighting function.

The averaged depolarization scores $D_{av}(j,k,l)$ form a volume that may be displayed as multiple 2D images corresponding to the B-scans of the PS-OCT volume. Each pixel (j,k) of the image represents the averaged depolarization score $D_{av}(j,k,l_{bscan})$ and is negative for pixels which are most likely to be depolarized, and positive for pixels most likely to be polarizing.

Figure 19A:
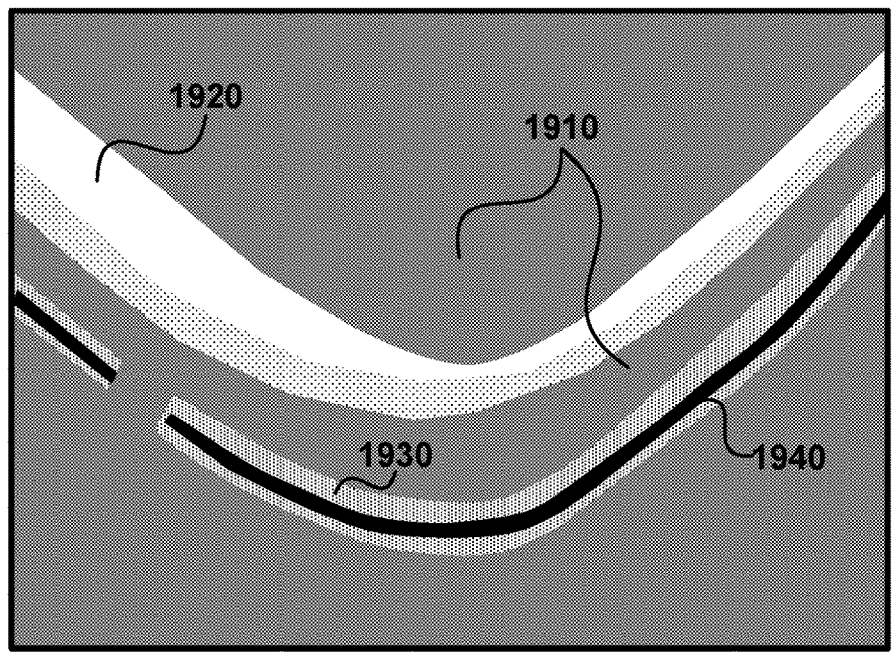
FIG. 19A is an example illustration of a depolarization score B-scan image, as calculated using the method of FIG. 9.

An example of such a depolarization score image for a single B-scan is shown in FIG. 19A, which builds upon the example of FIG. 5A. In this illustration, black indicates a negative depolarization score and white indicates a positive depolarization score. The background (1910) has a depolarization score close to zero, shown in mid-grey, as the backscattered signal is of low intensity in the background regions (1910) and there is insufficient evidence to determine the depolarization of the tissues in these regions. The upper retinal layers (1920), shown as white, and the outer limiting membrane (1930), shown as light-grey, have depolarization scores that are positive, as the backscattered signal is of high intensity and the tissues are polarization preserving. The RPE (1940) has depolarization scores that are negative and shown as black, as the backscattered signal is of high intensity and the tissues are polarization scrambling.

Calculating the Spatially Varying Mean Direction

For measurements obtained from a PS-OCT system, the dominant polarization direction of the polarization changes with spatial position in the PS-OCT volume. The assumption that the dominant polarization direction is constant for each A-scan is made based on the physical assumption that the retina is only weakly birefringent and the measured axis orientation should not change with depth in the retina. The change of the polarization direction with lateral position in the retinal OCT is due to the birefringence of the anterior segment of the eye. Note that in the case that there is significant birefringence in the retina, a local dominant polarization direction can be calculated over contiguous regions in the scan.

The estimated polarization direction is preferably determined according to the method 1000 of FIG. 10. The method (1000) is preferably implemented in software executable upon the processor 205 and operates upon previously acquired PS-OCT measurements in a scan volume provided as polarization measurements represented as the vectors P(j,k,l) and intensity measurements represented as the values I(j,k,l) where j∈{1, 2, . . . , $N_x$} indexes the x-direction, k∈{1, 2, . . . , $N_y$} indexes the y-direction, and l∈{1, 2, . . . , $N_z$} index the z-direction. Here the z-direction corresponds to the direction of an A-scan, the x-direction corresponds to the orthogonal direction used to capture a B-scan, and the y-direction corresponds to the direction used to capture successive B-scans, as illustrated in FIGS. 3A to 3C. The method (1000) stores the estimated dominant polarization direction at each A-scan in the array μ*(j,k) where j and k are the indices of the A-scan.

In step (1010) the next A-scan from the volume is selected by the processor (205), as specified by the indices (j,k). In the next step (1020), the approximate concentration $\kappa_l$ is calculated for each pixel in the A-scan from the intensities I(j,k,l) using the intensity-concentration relationship previously calculated in the method (700) of FIG. 7. In step (1030) the weighted average polarization is calculated by the processor (250) summing the polarization vectors in the A-scan multiplied by the calculated concentration for the corresponding pixel, using the following equation:

$$P_{av}(l) \leftarrow \sum_{l=1}^{N_z} \kappa_l P(j, k, l). \tag{44}$$

In step (1040) the average polarization is normalized to give the estimated dominant polarization direction:

$$\mu^{(p)}(j, k) \leftarrow \frac{P_{av}(l)}{\|P_{av}(l)\|}. \tag{45}$$

This value is now stored in a volume array, for example in the memory 206 or HDD 210, with the same indexing as the original intensity and polarization data. Step (1050) then operates, whereby the processor (205) tests whether all A-scans have been processed. Where not, the method (910) returns to step (1010) for processing the next A-scan.

Finally, when all A-scans have been processed, as determined at step (1050), the final direction estimate is calculated in step (1060) by the processor (205) as a weighted average of the volume data over appropriate range of data in the x-direction and the y-direction, using the following equation:

$$\mu^*(j, k) \leftarrow \frac{1}{W} \sum_{u=-m}^{m} \sum_{v=-m}^{m} w(u, v) \mu^{(p)}(j+u, k+v), \tag{46}$$

where m is the range of data averaged over in the x and y directions, and W is the weighting normalization given by the following equation:

$$W = \sum_{u=-m}^{m} \sum_{v=-m}^{m} w(u, v), \tag{47}$$

The weights w(u,v) can be for example a Gaussian weighting, as given by the following equation:

$$w(u,v) \leftarrow \exp[-(u^2+v^2)/(2\sigma_a^2)], \tag{48}$$

where the width of the weighting function $\sigma_a$ is chosen to smooth the estimated values and give an estimate with spatially changes no more rapidly than expected. In experiments performed by the present inventors, a value of $\sigma_a=5$ was found to afford useful results. Other values of $\sigma_a$ may be used.

Figure 13:
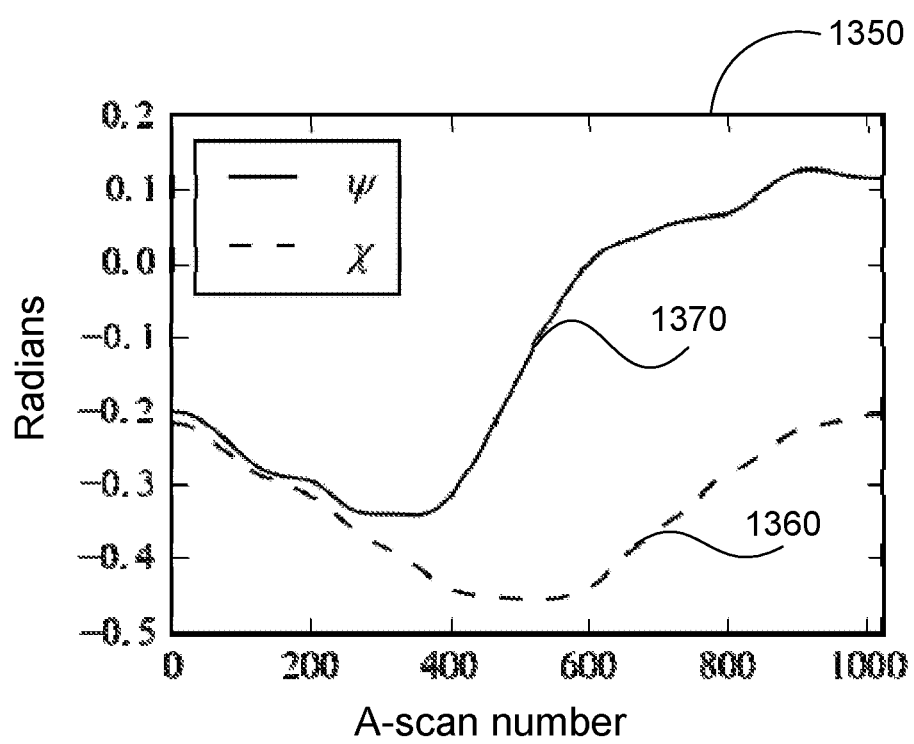
FIG. 13 is a graph showing the calculated estimated mean direction in an example B-scan from acquired PS-OCT data, as calculated in the method of FIG. 9.

An example of the calculation of the estimated dominant polarization direction in a single B-scan is shown in FIG. 13 which shows a graph (1350) of the elliptical angle, χ, shown as the line (1360), and the ellipticity of the polarization, ψ, shown as the line (1370) as a function of the A-scan number. These angles are related to the normalized Stokes parameters by Equation (3), as illustrated in FIG. 12.

Calculating the Depolarization Score Function

Figure 11:
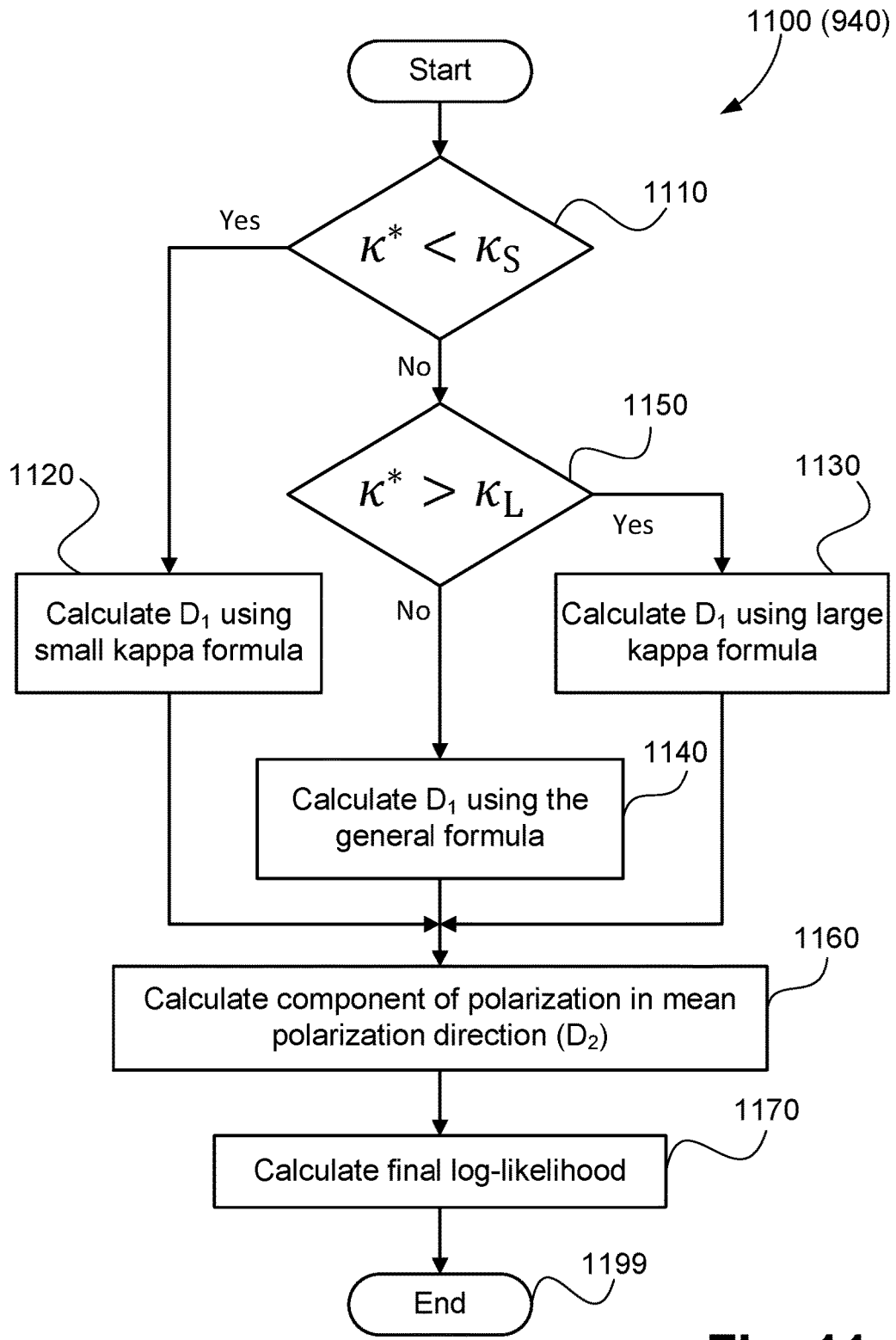
FIG. 11 is a schematic flow diagram illustrating a method of calculating the depolarization log-likelihood function from acquired PS-OCT data.

The depolarization score function, calculated in step (940), is preferably determined according to a method (1100) detailed with reference to FIG. 11. The method (1100) receives as input the polarization for a single sample, P=P(j,k,l), the estimated value of the dominant polarization direction, μ*, and the estimated value of the concentration, κ*. Firstly, the value of the term log C($\kappa_k$) in Equation (30) is calculated by the processor (250) using asymptotic forms for small and large values of the concentration parameter, $\kappa_k$.

In step (1110), the estimated value of the concentration κ* is tested to determine if it is below a (small) threshold, $\kappa_s$. A generally useful value for the threshold is $\kappa_s=10^{-3}$. If the value of the concentration κ* is below this threshold, the asymptotic formula of Equation (32) is then used in step (1120) by the processor (205) to evaluate the score function according to the following formula:

$$D_1 \leftarrow -\log(4\pi) - \log\left(1 + \frac{\kappa^{*2}}{6}\right). \quad (49)$$

The method (1100) then continues in step (1160).

Otherwise, where the concentration is above the small threshold, the method (1100) continues to step (1150), where the value of the concentration is tested to determine if it is above a (large) threshold, $\kappa_L$. A generally useful value for the large threshold is $\kappa_L$=10. If the value of $\kappa^*$ is above the large threshold, the asymptotic formula of Equation (33) is used by the processor (205) in step (1130) to evaluate the score function, as given by the following formula:

$$D_1 \leftarrow \log(\kappa^*) - \log(2\pi) - \kappa^*. \quad (50)$$

The method (1100) then continues in step (1160).

Otherwise, where steps (1110) and (1150) test that the concentration is between the small and large thresholds, the method (1100) continues to step (1140), where the general form of Equation (16) is used by the processor (205) to evaluate the score function, as given by the following formula:

$$D_1 \leftarrow \log(\kappa^*) - \log(2\pi) - \log[\exp(\kappa^*) - \exp(-\kappa^*)]. \quad (51)$$

The method (1160) then continues in step (1160).

In step (1160) the inner product of the input dominant polarization direction and the input polarization multiplied by the approximate concentration $\kappa^*$ is calculated by the processor (250), as given by the following formula:

$$D_2 \leftarrow \kappa^* \mu^{*T} P. \quad (52)$$

The term $\mu^{*T}P$ in Equation (52) results in an evaluation of a degree of divergence of the input polarization direction P from the dominant or reference polarization direction, $\mu^*$. The degree of divergence corresponds to a scalar value related to the angle between the dominant polarization direction and the input polarization direction.

In step (1170) the final log-likelihood score for the input data is calculated by the processor (250), as given by the following equation:

$$D(j,k,l) \leftarrow D_1 + D_2 + \log 4\pi, \quad (53)$$

where the value of $D_1$ was calculated in step (1120), (1130), or (1140) depending upon the magnitude of $\kappa^*$ and the value of $D_2$ was calculated in step (1160). Note that Equation (53) corresponds to the depolarization score function of Equation (30) for a single sample N=1 and with an uninformative prior of $\gamma$=0.

Classification of Depolarizing Regions

The classification of regions using previously acquired PS-OCT measurements as polarizing (i.e. likely to have come from polarization-preserving tissue), depolarizing (i.e. likely to have come from polarization-scrambling tissue), or uncertain, will now be explained with reference to the method (1800) shown in the flow diagram of FIG. 18. The method (1800) receives as input previously acquired PS-OCT measurements provided as N measurements of the polarization represented as the vectors $P_l$, where $l \in \{1, 2, \ldots, N\}$.

In step (1810) a depolarization score is calculated for each measurement from the previously acquired PS-OCT measurements, for example using the method (900) of FIG. 9, or alternatively the method (1600) of FIG. 16, described below. The calculation of a depolarization score $D_l$ is thus available for each measurement $l \in \{1, 2, \ldots, N\}$ from the previously acquired PS-OCT measurements. In step (1810), a counter l is also initialized to point to the first measurement, $l \leftarrow 1$.

Next, in step (1820) the next sample is selected according to the counter 1 and in step (1830) the depolarization value for the current measurement $D_l$ is compared by the processor (205) to a directional polarized score threshold $D_{T,D}$. For example, a threshold $D_{T,D}$=+0.5 can be used. If the value of the depolarization score is higher than the threshold $D_{T,D}$, control passes to step (1850) where the measurement is determined or deemed to be polarizing and the classification for the current measurement is set to one, $C_l \leftarrow 1$. The method (1800) then passes to step (1880).

Otherwise, where step (1830) determines that the value of the depolarization score is lower than the threshold $D_{T,D}$, the method (1800) continues to step (1840) where the depolarization value for the current measurement $D_l$ is compared to a depolarized score threshold $D_{T,U}$. For example, a threshold $D_{T,U}$=−0.5 can be used. If the value of the current depolarization score $D_l$ is lower than this threshold, control passes to step (1860) where the sample is deemed to be depolarizing and the classification for the current measurement is set to negative one, $C_l \leftarrow -1$. The method (1800) then passes to step (1880).

Otherwise, where the value of the current depolarization score $D_l$ is higher than the threshold $D_{T,U}$, the method continues to step (1870) where the measurement is deemed to be uncertain and the classification for the current measurement is set to zero, $C_l \leftarrow 0$. The method then also passes to step (1880).

After the sample or element of the data set has been classified, in step (1880) the counter, l, is compared to the number of measurements, N, to determine if all measurements have been computed. If l<N there are more measurements to calculate, and the counter is incremented, $l \leftarrow l+1$, and control returns to step (1820). Otherwise, the method of classifying (1800) terminates at step (1899) returning the determined classification for each input element as the values $C_l$ for $l \in \{1, 2, \ldots, N\}$. Where desired, the determined classification may be displayed by the processor (205) upon the display (214) for examination by an optical practitioner.

Figure 18:
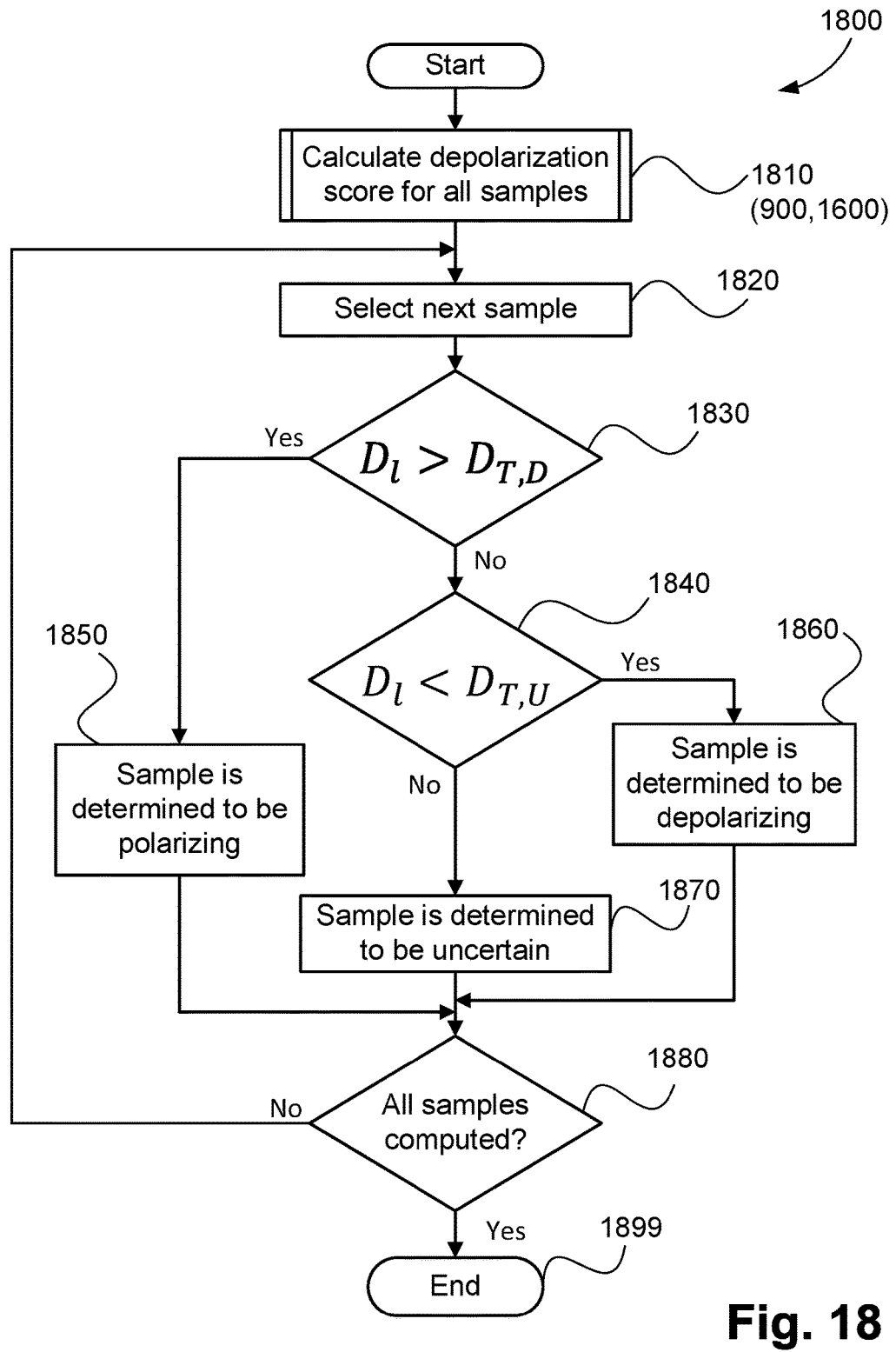
FIG. 18 is a schematic flow diagram illustrating a method of calculating a label that indicates if an areas has been determined to be polarization preserving or polarization scrambling (depolarizing)
Figure 19B:
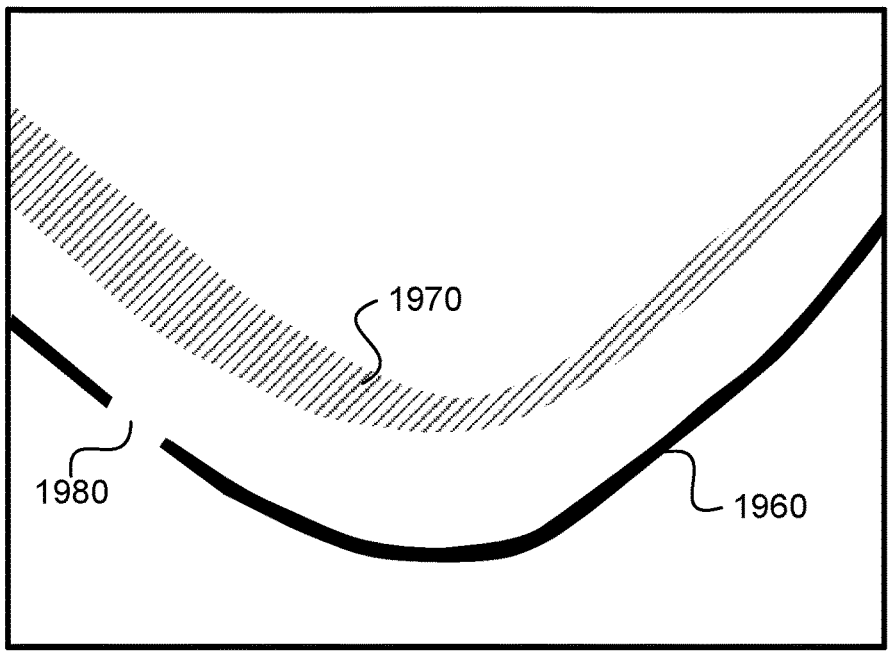
FIG. 19B is an example illustration of tissue identified according to the method of FIG. 18 as being depolarizing (polarization scrambling) using the depolarization score B-scan image of FIG. 19A.

An illustration of a possible classification using the method of FIG. 18 is shown in FIG. 19B, representative of the displayed classification. The method (1800) takes as input the depolarization scores illustrated in FIG. 19A. Consider the case that areas that are colored black have depolarization score values that are below the threshold value $D_{T,U}$, areas that are colored white in FIG. 19A have depolarization score values that are above the threshold value $D_{T,D}$. All other areas have depolarization score values that are between the two threshold values $D_{T,U}$, and $D_{T,D}$.

The areas that have a depolarization score below than the threshold value $D_{T,U}$ are determined to be depolarizing (1960) by the method (1800) shown in FIG. 18 and are given a class $C_l$=1 and displayed in FIG. 19B as black. The areas that have a depolarization score greater than the threshold value $D_{T,D}$ are determined to be polarizing (1970) and are given a class $C_l$=−1 and displayed in FIG. 19B as a hashed area. All other regions are determined to be uncertain and are given a class $C_l$=0 and are displayed in FIG. 19B as white.

The processing described above that results in the image representation of FIG. 19B now clearly shows the difference between polarization-maintaining and polarization-scrambling tissues in the retina. Such an image can be used to assist in the diagnosis of diseases of the retinal pigment epithelium, including age-related macular degeneration.

The classification into three classes can also assist the user to distinguish a region where there is a low intensity signal, such as the shadowed area (1980), from an area of high intensity polarization-preserving tissue. Shadowed areas can result from occlusion by a blood vessel (535) such as that illustrated in FIG. 5A.

Second Implementation

Instead of using theoretical distributions to approximate the polarization distributions of polarization-preserving and depolarizing (polarization-scrambling) tissues, learned density estimates can be used to calculate the likelihood ratio of Equation (28).

Figure 15:
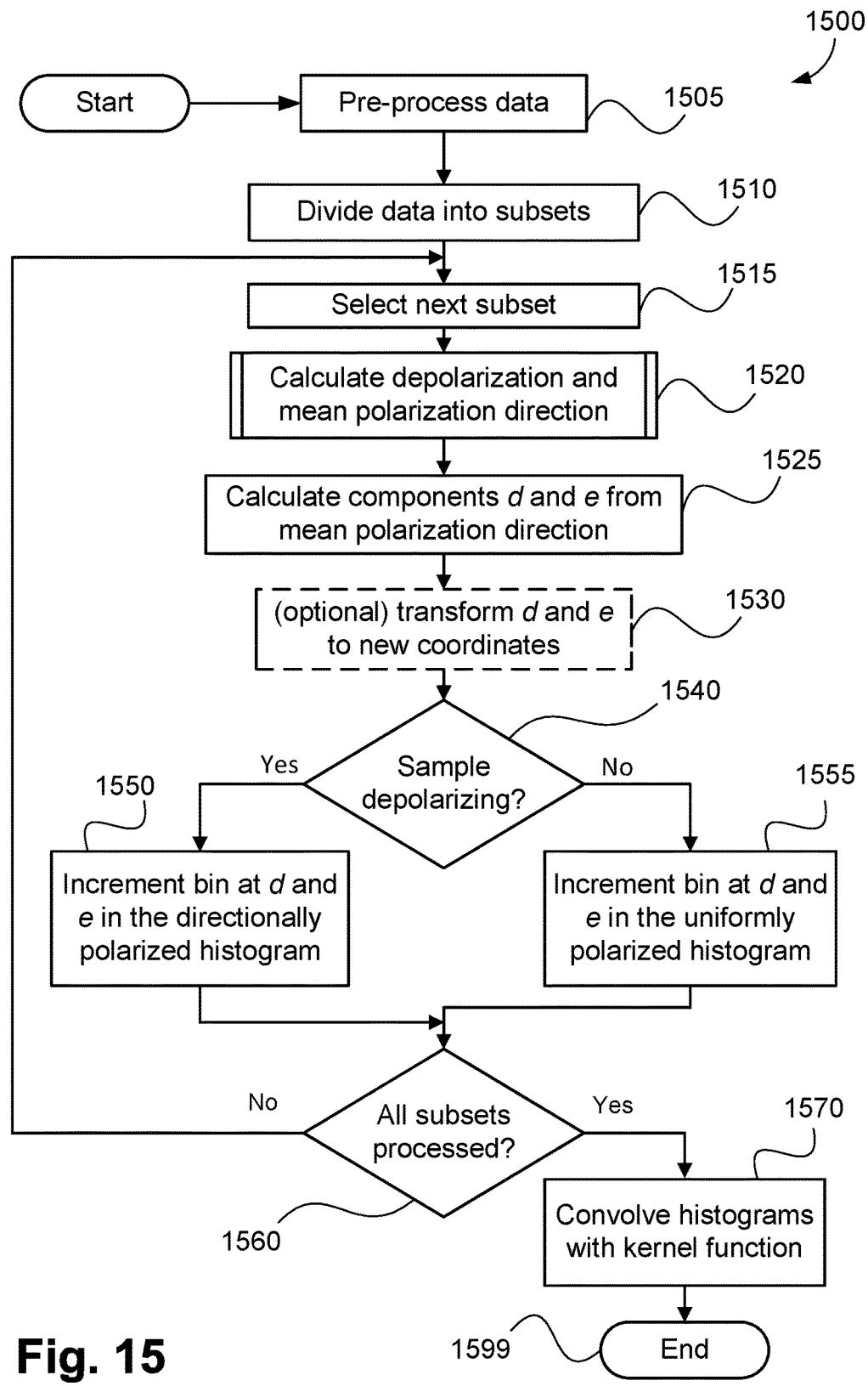
FIG. 15 is a schematic flow diagram illustrating a method of empirically determining the histograms of statistics of polarization-preserving and polarization-scrambling tissues from acquired PS-OCT data.

A method (1500) of learning the polarizing distribution and the depolarizing distribution is illustrated in FIG. 15. The method (1500) is desirably implemented by software stored in the HDD (210) and executed by the processor (205) and is input with previously acquired PS-OCT intensity measurements and polarization measurements. This may consist of multiple data sets from different patients, with each data set being the PS-OCT data elements captured that represents a volume of the retina.

In a pre-processing step (1505), the histograms representing the polarized and depolarized distributions are initialized to zero. The histogram stores the count of measurements in the axes $(\tilde{d}, \tilde{e})$ which are the transformed polarization components normal to and orthogonal to an estimated dominant polarization direction. Each histogram contains $N_1 \times N_2$ elements representing the division of the expected limits of the transformed polarization components $\tilde{d}$ and $\tilde{e}$. Each data element (j,k) in a histogram represents the bin containing samples from all transformed polarization components $(\tilde{d}, \tilde{e})$ in the range $d_j < \tilde{d} \leq d_{j+1}$ and $e_k < \tilde{e} \leq e_{k+1}$ where $j \in [0, 1, \ldots, N_1-1]$ and $k \in [0, 1, \ldots, N_2-1]$. The element (j,k) in the histogram representing the directionally polarized distribution is given the notation $H_D(j,k)$ and in the histogram representing the depolarized distribution is given the notation $H_U(j,k)$.

At step (1510) the input PS-OCT data is divided into one or more subsets denoted $S_1, \ldots, S_K$, where K is the number of subsets. These subsets may be chosen to be individual B-scans of the previously acquired PS-OCT volumes. At step (1510), a subset counter is also initialized to the first subset, $k \leftarrow 1$.

At step (1515) the next subset, $S_k$, is chosen and this data is used in the following calculations to step (1560). The subset $S_k$ includes L samples of intensity and polarization, denoted by the set of L intensity samples, $\{I_1, \ldots, I_L\}$, and the set of L polarization samples, $\{P_1, \ldots, P_L\}$.

In step (1520) a depolarization estimate $D_l$ is calculated by the processor (250) for all samples $l \in [1 \ldots L]$ in the current subset, which can be used later to include only samples that likely come from a directionally polarized distribution. The calculation of depolarization can be preferably performed by the method (1000) of FIG. 10, or the method (1600) of FIG. 16, or alternatively another technique such as DOPU can be used. Additionally, the dominant polarization direction $\mu^*_l$ is calculated by the processor (250) for all samples $l \in [1 \ldots L]$ with reference to the method (1000) of FIG. 10.

In step (1525) the polarization and intensity measurements for the current subset $S_k$ are transformed by the processor (205) to components parallel and orthogonal to the dominant polarization direction, written as $d_l$ and $e_l$ respectively, where only the magnitude of the component orthogonal to the dominant polarization direction $\mu^*_l$ is kept. This is due to the fact that the distribution of polarization is expected to be rotationally invariant about the dominant polarization direction.

$$d_l \leftarrow I_l \mu^*_l \cdot P_l,$$

$$e_l \leftarrow \|I_l P_l - d_l \mu^*_l\|. \tag{54}$$

In step (1530) the polarization concentration components $(d_l, e_l)$ are optionally transformed by the processor (205) to a nonlinear space so that the histogram is more finely sampled in regions of expected dense data. The present inventors have found that an appropriate transformation is given by the following, $$\tilde{d}_l \leftarrow d_l, \quad \tilde{e}_l \leftarrow 20 e_l^{0.4}. \tag{55}$$

In step (1540) the sample is determined by the processor (205) to be most likely from a directionally polarized or a depolarized distribution based on the depolarization value $D_l$. The sample is determined to be depolarized if the depolarization value $D_l$ is lower than a threshold value $D_{th}$, and directionally polarized if it is greater than the threshold value $D_{th}$. Alternatively, two threshold values may be used, and uncertain values between these two thresholds can be ignored.

If the sample is determined to be likely from polarization-maintaining tissue, the method (1500) continues to step (1550) where the sample is selected and the directionally polarized histogram $H_D$ is updated for a directionally polarized subset of elements of the test data set. The histogram bin to be updated is found such that $d_j < \tilde{d}_l \leq d_{j+1}$ and $e_k < \tilde{e}_l \leq e_{k+1}$ for some location (j,k). This element in the directionally polarized histogram is then incremented such that $H_D(j,k) \leftarrow H_D(j,k) + 1$. The method then continues to step (1560).

If the sample is determined to be likely from polarization-scrambling tissue at step (1540), the method (1500) continues to step (1555) where the sample is selected for updating the depolarized histogram $H_U$ for a depolarized subset of elements of the test data set. The histogram bin to be updated is found such that $d_j < \tilde{d}_l \leq d_{j+1}$ and $e_k < \tilde{e}_l \leq e_{k+1}$ for some location, (j,k). This element in the depolarized histogram is then incremented, $H_U(j,k) \leftarrow H_U(j,k) + 1$. The method (1500) then continues to step (1560).

In step (1560) the data subset counter, k, is compared to the number of subsets, K, to determine if all data subsets have been computed, $k \geq K$. If there are more subsets to compute, the data subset counter is incremented, $k \leftarrow k+1$, and control returns to step (1515). Otherwise, the method (1500) continues to step (1570).

In step (1570) the histograms are convolved with a kernel function by the processor (205) to produce an approximated kernel density estimate for the polarization data. A typical kernel function is the Gaussian kernel of a width chosen so that the density estimate is not over-smoothed or under-smoothed. A good estimate is given by Silverman's rule of thumb, namely $$h = \left(\frac{4\sigma^5}{3n}\right)^{1/5}$$

where n is the number of samples, $\sigma$ is the empirical standard deviation and h is the bandwidth of the Gaussian kernel.

Finally, in step (1599) the method (1500) terminates returning the smoothed histograms $H_D$ and $H_U$ representative of the polarizing distribution and the depolarizing distribution, respectively.

The results of the method (1500) of FIG. 15 using previously captured PS-OCT data is shown in the graphs of FIGS. 17A and 17B. The resulting histograms $H_D$ and $H_U$ are shown as the directionally polarized (1710) and depolarized (1700) graphs where the density of the shading corresponds to the density of the histogram at that point, as indicated by the legend. The histogram for depolarized data (1700) of FIG. 17A and the histogram for directionally polarized data (1710) of FIG. 17B are seen to be quite different. This difference is required for good discrimination between polarization-maintaining and polarization-scrambling (depolarizing) tissues.

Figure 14B:
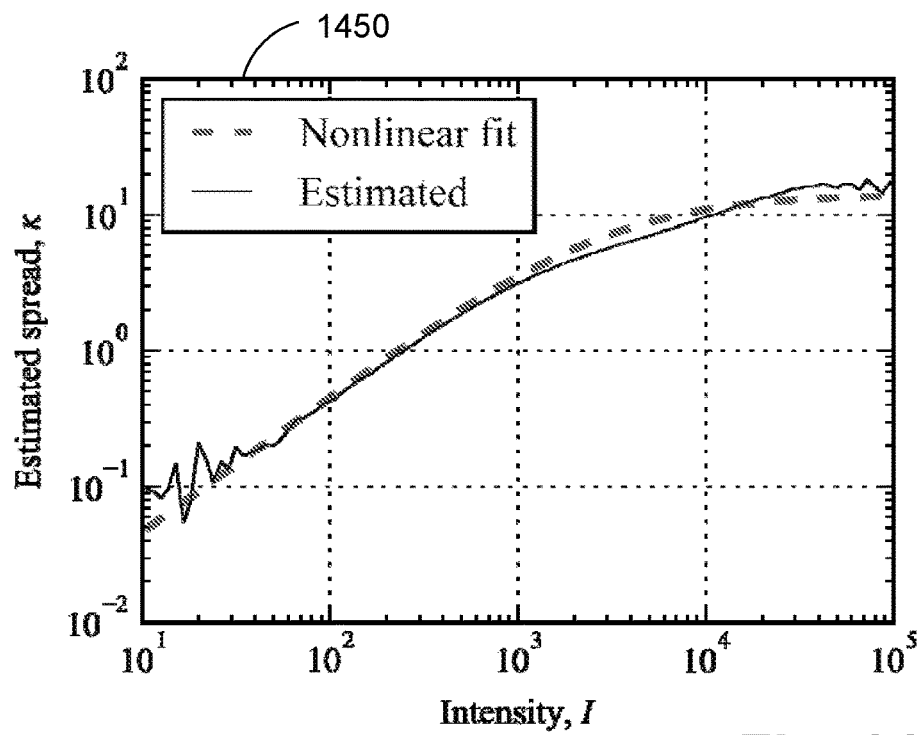
FIG. 14B is a graph showing the empirical relationship between polarization concentration and intensity for a particular depolarization masking level and a fitted functional relationship from acquired PS-OCT data, as calculated in the method of FIG. 7.

The above notwithstanding, the histograms of FIGS. 17A and 17B can be approximated by assuming that the data can be accurately determined to be from either a directionally polarized or a depolarized distribution. In practice this is not the case; therefore, the calculated histograms are likely to be a mixture of data from both regions. To determine the effect of inaccuracies in the determination of these regions, synthetic data is drawn from the von-Mises Fisher (directionally polarized) distribution or the uniform (depolarized) distribution to give a test or synthetic data set. This synthetic data set is generated using the same intensity information as the histograms shown in FIGS. 17A and 17B, but the polarization data is generated using the theoretical von-Mises Fisher distribution of Equation (14) for the directionally polarized histogram and the uniform distribution of Equation (17) for the depolarized histogram. Additionally, the concentration parameter $\kappa$ for the von-Mises-Fisher distribution was calculated using Equation (35) with values of the parameters given by $\alpha_1 = 4.6 \times 10^{-3}$ and $\alpha_0 = 7.1 \times 10^{-2}$, as shown in FIG. 14B.

The histograms generated using this synthetic polarization data are shown in FIGS. 17C and 17D. The histograms of FIGS. 17C and 17D using the von-Mises Fisher and uniform distributed data are very similar to the histograms calculated from real data of FIGS. 17A and 17B respectively. The histogram of FIG. 17D for synthetic uniformly polarized data (1720) is seen to be symmetric in reflection about the vertical axis, $\tilde{d}=0$, whereas the histogram of FIG. 17B for real data from likely depolarizing regions (1700) is tilted and has a higher probability of data with positive $\tilde{d}$. Apart from this difference the respective histograms for real and synthetic data are very similar, leading to the conclusion that the potential mixing between samples from polarization-maintaining and polarization-scrambling tissues in the real data doesn't greatly affect the resulting histograms.

Calculating the Depolarization Score

Figure 16:
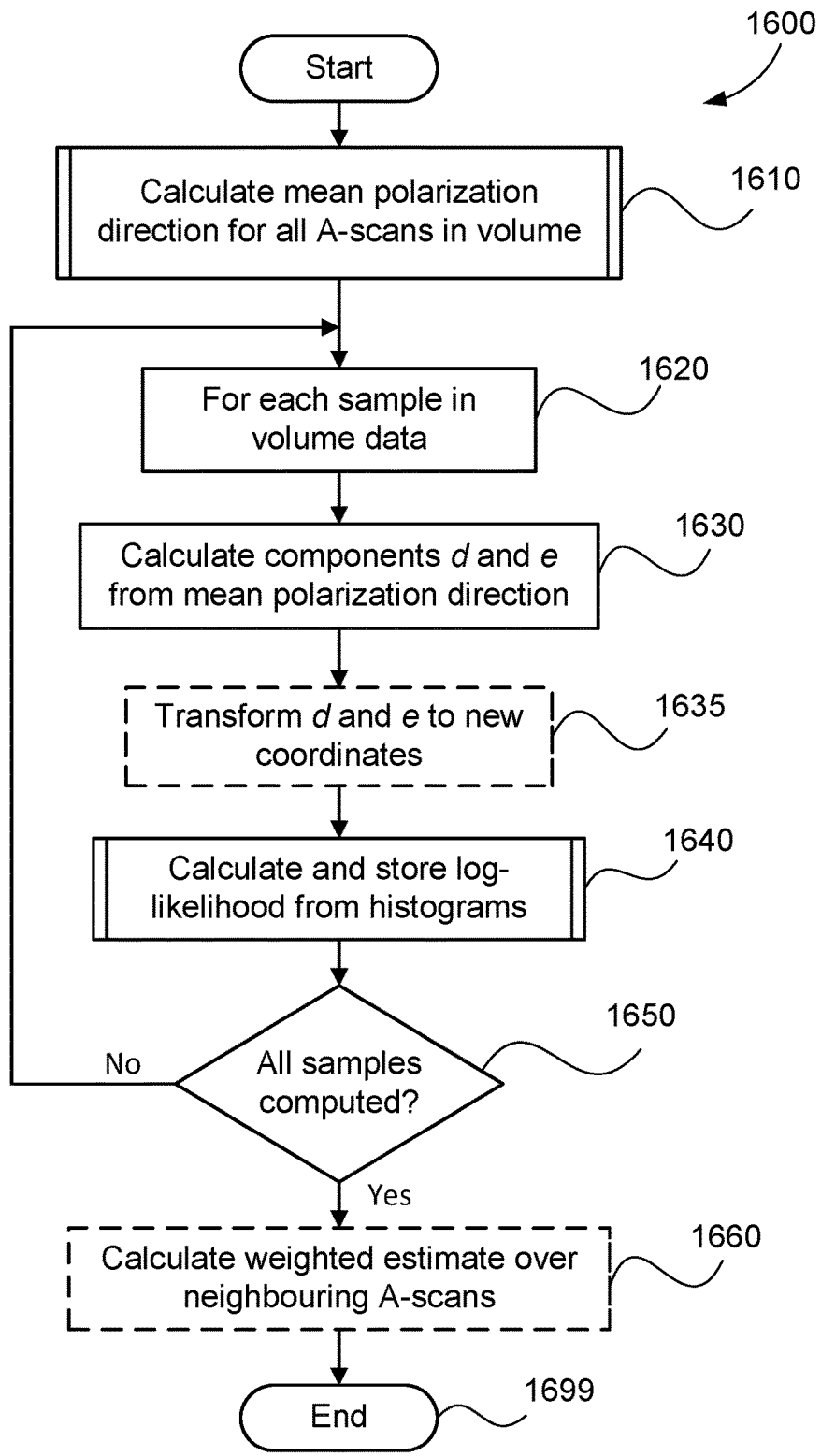
FIG. 16 is a schematic flow diagram illustrating a method of calculating a depolarization score from acquired PS-OCT data and pre-calculated polarization-preserving and polarization-scrambling histogram data.

The depolarization score can be calculated according to a method (1600) shown in FIG. 16. The method (1600), which represents an alternative implementation of step (720), operates upon previously acquired PS-OCT data provided as a volume of the polarization represented as the vectors P(j,k,l), and the intensity represented as the values I(j,k,l) where $j \in \{1, 2, \ldots, N_x\}$ indexes the x-direction, $k \in \{1, 2, \ldots, N_y\}$ indexes the y-direction, and $l \in \{1, 2, \ldots, N_z\}$ index the z-direction. Here the z-direction corresponds to data from a single A-scan, the x-direction corresponds to data from a single B-scan, and the y-direction corresponds to data from different B-scans, as illustrated in FIGS. 3A to 3C. Additionally, two density estimates are received by the method (1600) as the matrices $H_D$ and $H_U$ which have been calculated as per the method (1500) of FIG. 15. Each histogram contains $N_1 \times N_2$ elements, where $N_1$ and $N_2$ jointly represent the division of the expected limits of the transformed polarization components $\tilde{d}$ and $\tilde{e}$. Each element (m,n) in $H_D$ and $H_U$ represents the estimated density of polarization components $(\tilde{d}, \tilde{e})$ in the range $d_m < \tilde{d} \le d_{m+1}$ and $e_n < \tilde{e} \le e_{n+1}$ where $m \in [0, 1, \ldots, N_1]$ and $n \in [0, 1, \ldots, N_2]$.

The histograms $H_D$ and $H_U$ are used as approximations to the density functions $f_D$ and $f_U$ respectively in the Bayesian log-likelihood ratio of Equation (28). It is noted that as these distributions are learnt from a ground truth classification of real data. As a consequence, low-intensity regions are determined to be directionally polarized because they are labelled as such in the ground truth.

In step (1610) the estimated dominant polarization direction $\mu^*(j,k)$ is calculated by the processor (250) for all A-scans in the provided PS-OCT volume data. This may be performed according to the method (1000) of FIG. 10. In step (1610), the volume indices (j,k,l) are also initialized to point to the first sample in the volume.

In step (1620) the next sample from the volume data is selected, as specified by the indices (j,k,l). In the next step (1630), the estimated polarization components (d,e) are calculated by the processor (205) for the current sample using the intensity I(j,k,l) and polarization P(j,k,l) using the following equations:

$$d \leftarrow I(j,k,l)\mu^*(j,k) \cdot P(j,k,l),$$

$$e \leftarrow \|I(j,k,l)P(j,k,l) - d\mu^*(j,k)\|. \quad (56)$$

In step (1630) the polarization concentration components (d,e) are optionally transformed to a nonlinear space to match the sampling of the histogram in the method (1500) of FIG. 15.

An appropriate transformation is given by the following, $$\tilde{d} \leftarrow d, \ \tilde{e} \leftarrow 20 e^{0.4}. \quad (57)$$

Next, in step (1640) the depolarization log-likelihood function of Equation (30) is calculated by the processor (250) for the current sample and stored in the depolarization score volume D(j,k,l), for example in the memory (206) or the HDD (210). The histogram element is found such that $d_m < \tilde{d} \le d_{m+1}$ and $e_m < \tilde{e} \le e_{n+1}$ for some location (m,n). The depolarization log-likelihood function is then calculated by the processor (250) from Equation (28) where the densities are approximated by the histograms and an uninformative prior of $\gamma = 0$ is taken, as given in the following equation:

$$D(j,k,l) \leftarrow \log [H_U(m,n) + \epsilon] - \log [H_D(m,n) + \epsilon], \quad (58)$$

In Equation (58) a small parameter $\epsilon$ is introduced to control the behaviour of the depolarization score in the case where there are few samples in the histogram. The value of the small parameter is chosen to be a number such that the histograms bins with values greater than the number are considered to be well sampled. When the number of samples in both histograms is less than the value of the small parameter then there is insufficient evidence to determine a sample as depolarizing or polarizing and a value close to zero will be returned the by method.

Next, in step (1650), the processor (205) determines if there are more samples to be computed in the volume, whereupon the volume indices are incremented to point to the next sample and control passes back to step (1620). Otherwise, the method (1600) may end, or optionally continue to step (1660). Where ended, the method (1600) results in stored log-likelihood values for each of the histograms in the input data.

Optionally, in step (1660), a final depolarization score is calculated by the processor (250) from the depolarization scores stored by step (1640). The final depolarization score is a weighted average of the depolarization score values D(j,k,l) over an appropriate range of data in the x-direction, the y-direction, and the z-direction using the following equation:

$$D_{av}(j, k, l) \leftarrow \frac{1}{W} \sum_{t=-M_t}^{M_t} \sum_{u=-M_u}^{M_u} \sum_{v=-M_v}^{M_v} w(t, u, v)D(j+t, k+u, l+v), \quad (59)$$

where an the weighting normalization, W, is given by the following equation:

$$W = \sum_{t=-M_t}^{M_t} \sum_{u=-M_u}^{M_u} \sum_{v=-M_v}^{M_v} w(t, u, v). \quad (60)$$

The weights w(t,u,v) can be a Gaussian weighting, as given by the following equation:

$$w(t,u,v) \leftarrow \exp[-(t^2+u^2+v^2)/(2 6\sigma_s^2)], \quad (61)$$

where the width $\sigma_s$ of the weighting function is chosen so that depolarization score values are averaged over a volume that is representative of the minimum likely size of depolarizing features expected in the retina. In this case, an appropriate range for the summation of Equation (59) may be taken to be four times the width of the weighting function, $M_t=M_u=M_v=4\sigma_s$.

Conclusion

The arrangements described provide for the processing of polarization-sensitive image data of the eye for the highlighting of particular structures and pathology, thereby facilitating diagnosis and consequential treatment.

INDUSTRIAL APPLICABILITY

The arrangements described are applicable to the computer and data processing industries and particularly for the processing of polarization sensitive image data of the eye.

The foregoing describes only some embodiments of the present invention, and modifications and/or changes can be made thereto without departing from the scope and spirit of the invention, the embodiments being illustrative and not restrictive.

The invention claimed is:

1. A computer-implementable method of analysing tissues of a retina, the method comprising:
receiving a polarization-sensitive (PS-OCT) image data set of the retina from a polarization-sensitive device, each element in the polarization-sensitive image data set being associated with an intensity value ($\{I_1, \ldots, I_L\}$) and a polarization direction ($\{P_1, \ldots, P_L\}$);
determining a likelihood score for each element of the polarization-sensitive image data set based on the intensity value of the element and a degree of divergence ($\mu^{*T}P$ or $D_2$) of the polarization direction associated with the element from a reference polarization direction ($\mu^*$) associated with the polarization sensitive image data set, wherein the likelihood score indicates whether said element is drawn from a directionally polarized distribution or a depolarizing distribution; and
classifying elements of the polarization-sensitive image data set using the determined likelihood scores to analyse tissues of the retina.

2. The method of claim 1, further comprising displaying a representation of the classified elements of the polarization-sensitive image data.

3. The method of claim 1, wherein the reference polarization direction is a dominant polarization direction determined by determining normalized average of polarization directions associated with the elements in the polarization-sensitive image data set.

4. The method of claim 1, wherein the polarizing distribution is characterised by a predetermined probability density distribution function having at least one control parameter dependent on an intensity value (I) of the element, the control parameter defining the concentration ($\kappa$) of the polarizing distribution.

5. The method of claim 4, wherein dependence of the control parameter on the intensity value is determined by fitting a function to estimated values of the control parameter ($\kappa^*$) for a plurality of polarization-sensitive images having different intensity parameters.

6. The method of claim 5, wherein the control parameters are stored in memory in association with corresponding intensity values.

7. The method of claim 1, further comprising determining the polarizing distribution using intensity values of the elements of the polarization-sensitive image data set and the reference polarization direction associated with the polarization-sensitive image data set.

8. The method of claim 1, wherein the polarization direction is determined by weighting polarization data associated with the element based on corresponding intensity value.

9. The method of claim 1, further comprising smoothing the likelihood scores in the classified polarization-sensitive image data set using a linear filter.

10. The method of claim 1, wherein the polarization-sensitive image data set is formed by a plurality of A-scans, each of which representing imaging signal produced by an polarization-sensitive device capable of penetrating beyond the retinal pigment epithelium (RPE) of the eye.

11. The method of claim 1, wherein the polarization-sensitive image data set represents a region in a B-scan corresponding to a subset of A-scans which form the B-scan.

12. The method of claim 1, wherein the polarization-sensitive image data set corresponds to a single A-scan, and the mean polarisation direction is determined as a sliding window over a plurality of neighbouring A-scans.

13. The method of claim 1, wherein the directionally polarized distribution is determined (1500) by selecting, from a test polarization-sensitive image data set, a first subset of elements associated with the likelihood score exceeding at least a first predetermined threshold.

14. The method of claim 1, wherein the depolarizing distribution is determined by selecting, from the test polarization-sensitive image data set, a second subset of elements associated with the likelihood score below a second predetermined threshold.

15. A system for analysing tissues of a retina, the system comprising:
a memory for storing data and a computer program;
a processor coupled to the memory for storing data and a computer program, the computer program comprising instructions for:
receiving a polarization-sensitive (PS-OCT) image data set of the retina from a polarization-sensitive device, each element in the polarization-sensitive image data set being associated with an intensity value ($\{I_1, \ldots, I_L\}$) and a polarization direction ($\{P_1, \ldots, P_L\}$);

determining a likelihood score for each element of the polarization-sensitive image data set based on the intensity value of the element and a degree of divergence ($\mu^{*T}P$ or $D_2$) of the polarization direction associated with the element from a reference polarization direction ($\mu^*$) associated with the polarization sensitive image data set, wherein the likelihood score indicates whether said element is drawn from a directionally polarized distribution or a depolarizing distribution; and classifying elements of the polarization-sensitive image data set using the determined likelihood scores to analyse tissues of the retina.

16. An apparatus for analysing tissues of a retina, the apparatus comprising:

means for receiving a polarization-sensitive (PS-OCT) image data set of the retina from a polarization-sensitive device, each element in the polarization-sensitive image data set being associated with an intensity value ($\{I_1, \ldots, I_L\}$) and a polarization direction ($\{P_1, \ldots, P_L\}$);

means for determining a likelihood score for each element of the polarization-sensitive image data set based on the intensity value of the element and a degree of divergence ($\mu^{*T}P$ or $D_2$) of the polarization direction associated with the element from a reference polarization direction ($\mu^*$) associated with the polarization sensitive image data set, wherein the likelihood score indicates whether said element is drawn from a directionally polarized distribution or a depolarizing distribution; and means for classifying elements of the polarization-sensitive image data set using the determined likelihood scores to analyse tissues of the retina.

17. A computer readable medium having a computer program stored thereon for analysing tissues of a retina, the program comprising:

code for receiving a polarization-sensitive (PS-OCT) image data set of the retina from a polarization-sensitive device, each element in the polarization-sensitive image data set being associated with an intensity value ($\{I_1, \ldots, I_L\}$) and a polarization direction ($\{P_1, \ldots, P_L\}$);

code for determining a likelihood score for each element of the polarization-sensitive image data set based on the intensity value of the element and a degree of divergence ($\mu^{*T}P$ or $D_2$) of the polarization direction associated with the element from a reference polarization direction ($\mu^*$) associated with the polarization sensitive image data set, wherein the likelihood score indicates whether said element is drawn from a directionally polarized distribution or a depolarizing distribution; and code for classifying elements of the polarization-sensitive image data set using the determined likelihood scores to analyse tissues of the retina.

18. A computer-implementable method of determining physical properties of tissues of a retina, the method comprising:

receiving a polarization-sensitive image data set of the retina from a polarization-sensitive device, each element in the polarization-sensitive image data set being associated with an intensity value and polarization data;

determining, for each element of the polarization-sensitive image data set, a likelihood score (D) that said element is drawn from a polarization scrambling signal based on a reference polarization direction ($\mu^*$) associated with the polarization-sensitive image data set, the intensity value and the polarization data of the element; and classifying the elements of the polarization-sensitive image data set using the determined likelihood scores to determine physical properties of tissues of the retina.

* * * * *